United States Patent
Lumbroso et al.

(10) Patent No.: US 11,136,292 B2
(45) Date of Patent: Oct. 5, 2021

(54) PLANT GROWTH REGULATOR COMPOUNDS

(71) Applicant: SYNGENTA PARTICIPATIONS AG, Basel (CH)

(72) Inventors: Alexandre Franco Jean Camille Lumbroso, Stein (CH); Alain De Mesmaeker, Stein (CH); Claudio Screpanti, Stein (CH); Stefano Rendine, Stein (CH)

(73) Assignee: SYNGENTA PARTICIPATIONS AG, Stein (CH)

( * ) Notice: Subject to any disclaimer, the term of this patent is extended or adjusted under 35 U.S.C. 154(b) by 101 days.

(21) Appl. No.: 16/332,673

(22) PCT Filed: Sep. 5, 2017

(86) PCT No.: PCT/EP2017/072155
§ 371 (c)(1),
(2) Date: Mar. 12, 2019

(87) PCT Pub. No.: WO2018/050477
PCT Pub. Date: Mar. 22, 2018

(65) Prior Publication Data
US 2019/0330148 A1  Oct. 31, 2019

(30) Foreign Application Priority Data
Sep. 13, 2016 (GB) ..................... 1615544

(51) Int. Cl.
*A01N 43/08* (2006.01)
*A01N 43/12* (2006.01)
*A01N 43/16* (2006.01)
*C07D 407/12* (2006.01)
*C07D 409/12* (2006.01)
*A01N 43/30* (2006.01)
*C07D 307/60* (2006.01)
*C07D 207/38* (2006.01)
*A01N 43/36* (2006.01)
*A01N 43/54* (2006.01)
*A01N 43/76* (2006.01)
*C07D 307/58* (2006.01)
*C07D 403/12* (2006.01)
*C07D 413/12* (2006.01)

(52) U.S. Cl.
CPC .......... *C07D 207/38* (2013.01); *A01N 43/08* (2013.01); *A01N 43/12* (2013.01); *A01N 43/16* (2013.01); *A01N 43/30* (2013.01); *A01N 43/36* (2013.01); *A01N 43/54* (2013.01); *A01N 43/76* (2013.01); *C07D 307/58* (2013.01); *C07D 307/60* (2013.01); *C07D 403/12* (2013.01); *C07D 407/12* (2013.01); *C07D 409/12* (2013.01); *C07D 413/12* (2013.01)

(58) Field of Classification Search
None
See application file for complete search history.

(56) References Cited

U.S. PATENT DOCUMENTS

| 4,371,691 A | 2/1983 | Friedhofen et al. |
| 8,946,280 B2 | 2/2015 | De Mesmaeker et al. |

FOREIGN PATENT DOCUMENTS

| EA | 023571 B1 | 6/2016 |
| EP | 0023571 A1 | 2/1981 |
| EP | 2518062 A1 | 10/2012 |
| WO | 2015/061764 A1 | 1/2000 |
| WO | 2010/137662 A1 | 12/2010 |
| WO | 2016/193287 A1 | 12/2016 |

OTHER PUBLICATIONS

Zwanenburg Binne et al; "Strigolactone Analogues and Mimics Derived from Phathalimide, Saccharine, P-tolymalondialdehyde, Benzoic and Salicyclic Acid as Scaffolds"; Bioorganic & Medicinal Chemistry Pergamon, GB, vol. 19, No. 24; 2011-10-24; pp. 7394-7400.

Alinanuswe S. Mwakaboko et al; "Strigolactone Analogues with a D-Ring Modified at C-2"; European Journal of Organic Chemistry, vol. 2016, No. 21; Jul. 1, 2016; pp. 3495-3499.

(Continued)

*Primary Examiner* — John Pak
(74) *Attorney, Agent, or Firm* — Bakerhostetler; Toni-Junell Herbert

(57) ABSTRACT

The present invention relates to relates to novel strigolactone derivatives of formula (I), to processes for preparing these derivatives including intermediate compounds, to seeds comprising these derivatives, to plant growth regulator or seed germination promoting compositions comprising these derivatives and to methods of using these derivatives in controlling the growth of plants and/or promoting the germination of seeds.

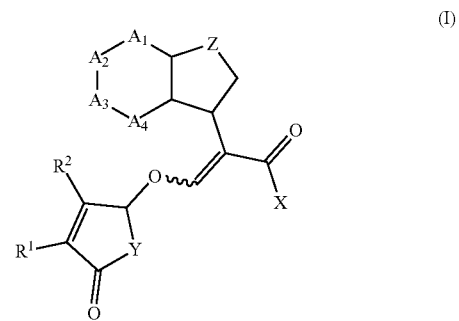

(I)

13 Claims, No Drawings

(56) References Cited

OTHER PUBLICATIONS

Mangnus et al.; "Structural Modifications Strigol Analogs. Influence of the B and C rings on the Bioactivity of the Germintion Stimulant GR24"; Journal of Agricultural and Food Chemistry, vol. 40, No. 7; 1992; pp. 1222-1229.

Daws et al; "Btenolide from Plant-Derived Smoke Functions as a Strigolactone Analogue: Evidence from Parasitic Weed Seed Germination"; South African Journal of Botany, vol. 74; 2008; pp. 116-120.

Great Britain Search Report of Application No. GB1615544.2 dated Jun. 13, 2017.

Belikov, V.G., Pharmaceutical chemistry, Part I. General pharmaceutical chemistry, 2007, pp. 27-29, MEDpress-inform, Moscow.

PLANT GROWTH REGULATOR COMPOUNDS

CROSS-REFERENCE TO RELATED APPLICATIONS

This application is a 371 National Stage application of International Application No. PCT/EP2017/072155, filed Sep. 5, 2017, which claims priority to Great Britain Application No. 1615544.2 filed Sep. 13, 2016, the entire contents of which applications are hereby incorporated by reference.

The present invention relates to relates to novel strigolactone derivatives, to processes for preparing these derivatives including intermediate compounds, to seeds comprising these derivatives, to plant growth regulator or seed germination promoting compositions comprising these derivatives and to methods of using these derivatives in controlling the growth of plants and/or promoting the germination of seeds.

Strigolactone derivatives are phytohormones which may have plant growth regulation and seed germination properties. They have previously been described in the literature. Certain known strigolactam derivatives may have properties analogous to strigolactones, e.g., plant growth regulation and/or seed germination promotion. WO2015/061764 discloses plant propagation materials comprising chemical mimics of strigolactone thought to be particularly effective under drought stress conditions.

The present invention relates to novel strigolactone derivatives that have improved properties. Benefits of the compounds of the present invention include improved tolerance to abiotic stress, improved seed germination, better regulation of crop growth, improved crop yield, and/or improved physical properties such as chemical, hydrolytic, physical and/or soil stability.

According to the present invention, there is provided a compound of formula (I)

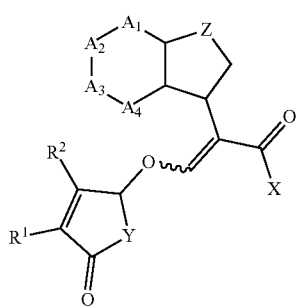

(I)

wherein
$R^1$ and $R^2$ are independently selected from the group consisting of hydrogen, $C_1$-$C_3$ alkyl and $C_1$-$C_3$ alkoxy;
X is $O(R^3)$ or $N(R^4R^5)$;
$R^3$ is selected from the group consisting of hydrogen, $C_1$-$C_4$ alkyl, $C_1$-$C_4$ alkenyl, $C_1$-$C_4$ alkynyl, $C_1$-$C_4$ alkoxy, $C_1$-$C_4$ alkoxycarbonyl, $C_4$-$C_7$ cycloalkyl, and phenyl;
$R^4$ and $R^5$ are independently selected from the group consisting of hydrogen, $C_1$-$C_4$ alkyl, $C_1$-$C_4$ alkenyl, $C_1$-$C_4$ alkynyl, $C_1$-$C_4$ alkoxy, $C_1$-$C_4$ alkoxycarbonyl, $C_4$-$C_7$ cycloalkyl, and phenyl; or $R^4$ and $R^5$ are joined to form a heterocycloalkyl;
Y is O or $N(R^6)$;
$R^6$ is aryl or aryl substituted by 1-4 $R^7$;
each $R^7$ is independently selected from the group consisting of halogen, $C_1$-$C_6$ alkoxy, hydroxyl, amine, N—$C_1$-$C_6$ alkylamine and N,N-di-$C_1$-$C_6$ alkylamine; or $R^7$ is selected from the group consisting of $C_1$-$C_6$ alkyl, $C_1$-$C_6$ alkenyl, $C_1$-$C_6$alkynyl, $C_1$-$C_8$alkylcarbonyl, $C_1$-$C_8$alkoxycarbonyl, $C_1$-$C_6$ cycloalkyl, heterocycloalkyl, aryl and heteroaryl each optionally substituted by halogen, $C_1$-$C_4$ alkyl or $C_1$-$C_4$ alkoxy;
Z is selected from the group consisting of a bond, $CH_2$, $CH_2$—$CH_2$, $CH_2$—$CH_2$—$CH_2$, (O)—$CH_2$, $CH(CH_3)_2$—$CH_2$, O and N;
$A_1$ to $A_4$ are each independently selected from the group consisting of a bond, $CR^8$, $CR^8$=$CR^8$, $C(R^8)_2$, $C(R^8)_2$—$C(R^8)_2$, N, $NR^8$, S and O, wherein $A_1$ to $A_4$ together with the atoms to which they are joined form a 4 to 7 membered cycloalkyl, heterocycloalkyl, aryl or heteroaryl; and
each $R^8$ is independently selected from the group consisting of hydrogen, halogen, $C_1$-$C_4$ alkyl, $C_2$-$C_4$ alkenyl, $C_2$-$C_4$ alkynyl, $C_1$-$C_4$ alkoxy and $C_1$-$C_4$ haloalkyl; or two $R^8$ groups are joined to form a 5-6 membered ring;
or salts thereof.

The compounds of the present invention may exist as different geometric isomers (Z or E isomer), optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of the present invention.

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups include $C_1$-$C_6$ alkyl, $C_1$-$C_4$ alkyl, and $C_1$-$C_3$ alkyl.

The term "alkenyl", as used herein, is an alkyl moiety having at least one carbon-carbon double bond, for example $C_2$-$C_6$ alkenyl. Specific examples include vinyl and allyl. The alkenyl moiety may be part of a larger group (such as alkenoxy, alkenoxy-carbonyl, alkenylcarbonyl, alkyenlaminocarbonyl, dialkenylaminocarbonyl).

The term "acetoxy" refers to —OC(=O)$CH_3$.

The term "alkynyl", as used herein, is an alkyl moiety having at least one carbon-carbon triple bond, for example $C_2$-$C_6$ alkynyl. Specific examples include ethynyl and propargyl. The alkynyl moiety may be part of a larger group (such as alkynoxy, alkynoxycarbonyl, alkynylcarbonyl, alkynylaminocarbonyl, dialkynylaminocarbonyl).

Halogen is fluorine (F), chlorine (Cl), bromine (Br) or iodine (I).

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Hydroxyalkyl groups are alkyl groups which are substituted with one or more hydroxyl group and are, for example, —$CH_2OH$, —$CH_2CH_2OH$ or —$CH(OH)CH_3$.

Alkoxyalkyl groups are an alkoxy group bonded to an alkyl (R—O—R'), for example —$(CH_2)_rO(CH_2)_sCH_3$, wherein r is 1 to 6 and s is 1 to 5.

In the context of the present specification the term "aryl" refers to a ring system which may be mono, bi or tricyclic. Examples of such rings include phenyl, naphthalenyl, anthracenyl, indenyl or phenanthrenyl.

Unless otherwise indicated, alkenyl and alkynyl, on their own or as part of another substituent, may be straight or branched chain and may contain 2 to 6 carbon atoms, and where appropriate, may be in either the (E) or (Z) configuration. Examples include vinyl, allyl, ethynyl and propargyl.

Unless otherwise indicated, cycloalkyl may be mono- or bi-cyclic, may be optionally substituted by one or more $C_1$-$C_6$ alkyl groups, and contain 3 to 7 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" refers to a ring system containing from one to four heteroatoms selected from N, O and S, wherein the nitrogen and sulphur atoms are optionally oxidized, and the nitrogen atom(s) are optionally quaternized. Heterocyclyl includes heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzo-furanyl, piperidinyl, 1,3-dioxolanyl, 1,3-dioxanyl, 4,5-dihydro-isoxazolyl, tetrahydrofuranyl and morpholinyl. In addition, the term "heterocyclyl" includes heterocycloalkyl, a non-aromatic monocyclic or polycyclic ring comprising carbon and hydrogen atoms and at least one heteroatom selected from nitrogen, oxygen, and sulfur such as oxetanyl or thietanyl. A monocyclic heterocycloalkyl may contain 3 to 7 members.

The term "heteroaryl" refers to an aromatic ring system containing from one to four heteroatoms selected from N, O, and S, wherein the nitrogen and sulfur atoms are optionally oxidized, for example having 5, 6, 9 or 10 members, and consisting either of a single ring or of two or more fused rings. Single rings may contain up to three heteroatoms, and bicyclic systems up to four heteroatoms, which will preferably be chosen from nitrogen, oxygen and sulfur. Examples of such groups include pyridyl, pyridazinyl, pyrimidinyl, pyrazinyl, furanyl, thienyl, oxazolyl, isoxazolyl, oxadiazolyl, thiazolyl, isothiazolyl, thiadiazolyl, pyrrolyl, pyrazolyl, imidazolyl, triazolyl and tetrazolyl.

Further definitions of $R^1$, $R^2$, X, $R^3$, $R^4$, $R^5$, Y, $R^6$, $R^7$, Z, $A_1$, $A_2$, $A_3$, $A_4$ and $R^8$ are, in any combination, as set out below.

$R^1$ and $R^2$ in compounds of the present invention are independently selected from the group consisting of hydrogen, $C_1$-$C_3$alkyl and $C_1$-$C_3$alkoxy. In one embodiment, $R^1$ and $R^2$ are independently selected from the group consisting of hydrogen, methyl, ethyl and methoxy. In a further embodiment, $R^1$ and $R^2$ are independently selected from the group consisting of hydrogen and methyl.

In one embodiment $R^1$ is methyl and $R^2$ is hydrogen or methyl. In a further embodiment, $R^1$ is methyl and $R^2$ is methyl.

X in compounds of the present invention is $O(R^3)$ or $N(R^4R^5)$.

In one embodiment X is $O(R^3)$, and $R^3$ is selected from the group consisting of hydrogen, $C_1$-$C_4$ alkyl, $C_1$-$C_4$ alkenyl, $C_1$-$C_4$ alkynyl, $C_1$-$C_4$ alkoxy, $C_1$-$C_4$ alkoxycarbonyl, $C_4$-$C_7$ cycloalkyl and phenyl. In one embodiment, $R^3$ is selected from the group consisting of hydrogen, $C_1$-$C_4$ alkyl, $C_1$-$C_4$ alkenyl, $C_1$-$C_4$ alkynyl and $C_1$-$C_4$ alkoxy. In a further embodiment, $R^3$ is selected from the group consisting of hydrogen and $C_1$-$C_4$ alkyl. In a further embodiment, $R^3$ is selected from the group consisting of hydrogen, methyl and ethyl.

In one embodiment X is OH. In a further embodiment X is O—$CH_3$. In a further embodiment, X is O—$C_2H_5$.

In a further embodiment X is $N(R^4R^5)$, and $R^4$ and $R^5$ are independently selected from the group consisting of hydrogen, $C_1$-$C_4$ alkyl, $C_1$-$C_4$ alkenyl, $C_1$-$C_4$ alkynyl, $C_1$-$C_4$ alkoxy, $C_1$-$C_4$ alkoxycarbonyl, $C_4$-$C_7$ cycloalkyl and phenyl; or $R^4$ and $R^5$ are joined to form a 4-7 membered heterocycloalkyl. In one embodiment, $R^4$ and $R^5$ are independently selected from the group consisting of hydrogen, $C_1$-$C_4$ alkyl, $C_1$-$C_4$ alkenyl, $C_1$-$C_4$ alkynyl and $C_1$-$C_4$ alkoxy, or $R^4$ and $R^5$ are joined to form a 4-7 membered heterocycloalkyl. In one embodiment $R^4$ and $R^5$ are independently selected from the group consisting of hydrogen and $C_1$-$C_4$ alkyl, or $R^4$ and $R^5$ are joined to form a 5-6 membered heterocycloalkyl. In one embodiment $R^4$ and $R^5$ are independently selected from the group consisting of hydrogen, methyl and ethyl, or $R^4$ and $R^5$ are joined to form a heterocyclopentyl ring.

In one embodiment, X is $NH_2$. In a further embodiment, X is $NH(CH_3)$. In a further embodiment, X is $N(CH_3)_2$.

Y in compounds of the present invention is O or $N(R^6)$.

In one embodiment Y is O.

In a further embodiment, Y is $N(R^6)$, wherein $R^6$ is aryl or aryl substituted by 1-4 $R^7$. In one embodiment, $R^6$ is phenyl optionally substituted by 1-4 $R^7$.

The aryl ring may be substituted at 0, 1, 2, 3 or 4 positions. The $R^7$ substitutions may be at any position on the aryl ring, for example at the ortho, meta or para position.

Each $R^7$ is independently selected from the group consisting of halogen, $C_1$-$C_6$ alkoxy, hydroxyl, amine, N—$C_1$-$C_6$ alkylamine and N,N-di-$C_1$-$C_6$ alkylamine; or $R^7$ is selected from the group consisting of $C_1$-$C_6$ alkyl, $C_1$-$C_6$ alkenyl, $C_1$-$C_6$alkynyl, $C_1$-$C_8$alkylcarbonyl, $C_1$-$C_8$alkoxycarbonyl, $C_1$-$C_6$ cycloalkyl, 4-7 membered heterocycloalkyl, 6 or 10 membered aryl and 5-6 or 9-10 membered heteroaryl each optionally substituted by halogen, $C_1$-$C_4$ alkyl or $C_1$-$C_4$ alkoxy.

In one embodiment each $R^7$ is independently selected from the group consisting of hydrogen, halogen, $C_1$-$C_6$ alkoxy, hydroxyl, amine, N—$C_1$-$C_6$ alkylamine and N,N-di-$C_1$-$C_6$ alkylamine; or $R^7$ is selected from the group consisting of $C_1$-$C_6$ alkyl, $C_1$-$C_6$ alkenyl, $C_1$-$C_6$alkynyl, $C_1$-$C_8$alkylcarbonyl and $C_1$-$C_8$alkoxycarbonyl each optionally substituted by halogen, $C_1$-$C_4$ alkyl or $C_1$-$C_4$ alkoxy.

In a further embodiment each $R^7$ is independently selected from the group consisting of hydrogen, halogen and $C_1$-$C_6$ alkoxy; or $R^7$ is selected from the group consisting of $C_1$-$C_6$ alkyl, $C_1$-$C_6$ alkenyl and $C_1$-$C_6$alkynyl each optionally substituted by halogen, $C_1$-$C_4$ alkyl or $C_1$-$C_4$ alkoxy.

In a further embodiment each $R^7$ is independently selected from the group consisting of hydrogen, halogen and $C_1$-$C_6$ alkyl.

In one embodiment Y is N-phenyl.

In a further embodiment Y is N-3,5-difluoro-phenyl.

Z in compounds of the invention is selected from the group consisting of a bond, $CH_2$, $CH_2$—$CH_2$, $CH_2$—$CH_2$—$CH_2$, (O)—$CH_2$, $CH(CH_3)_2$—$CH_2$, O and N.

In one embodiment Z is selected from the group consisting of a bond, $CH_2$, $CH_2$—$CH_2$, (O)—$CH_2$, and O.

In one embodiment Z is a bond, forming a cyclobutyl ring. In a further embodiment Z is $CH_2$, forming a cyclopentyl ring. In a further embodiment Z is $CH_2$—$CH_2$, forming a cyclohexyl ring. In a further embodiment Z is $CH_2$—$CH_2$—$CH_2$, forming a cycloheptyl ring. In a further embodiment Z is (O)—$CH_2$, forming a oxanering. In a further embodiment Z is an oxygen atom, forming a oxolane ring. In a further embodiment Z is a nitrogen atom, forming a pyrrolidine ring.

$A_1$ to $A_4$ in compounds of the invention are each independently selected from the group consisting of a bond, CR⁸, CR⁸=CR⁸, C(R⁸)₂, C(R⁸)₂—C(R⁸)₂, N, NR⁸, S and O, wherein $A_1$ to $A_4$ together with the atoms to which they are joined form a 4 to 7 membered cycloalkyl, heterocycloalkyl, aryl or heteroaryl; and each R⁸ is independently selected from the group consisting of hydrogen, halogen, $C_1$-$C_4$ alkyl, $C_2$-$C_4$ alkenyl, $C_2$-$C_4$ alkynyl, $C_1$-$C_4$ alkoxy and $C_1$-$C_4$ haloalkyl; or two R⁸ groups are joined via —OCH₂O— to form a 5-membered dioxolane ring.

In one embodiment $A_1$ to $A_4$ are joined to form a saturated or partially unsaturated ring. For example, $A_1$ to $A_4$ are joined to form a cycloalkyl ring such as cyclobutyl, cyclopentyl, cyclohexyl, cycloheptyl; or a heterocycloalkyl ring such as pyrrolidinyl, imidazolindinyl, pyrazolidinyl, oxazolidinyl, isoxazolidinyl, thiazolidinyl, isothiazolidinyl, piperidinyl, piperazinyl or morpholinyl.

In one embodiment $A_1$ to $A_4$ are joined to form an unsaturated ring. For example, $A_1$ to $A_4$ are joined to form an aryl ring such as phenyl; or a heteroaryl ring such as pyrrolyl, furanyl, thienyl, imidazolyl, pyrazolyl, oxazolyl, isoxazolyl, thiazolyl, isothiazolyl, oxadiazolyl, thiadiazolyl, triazolyl, tetrazolyl, pyridyl, pyrazinyl, pyrimidinyl or pyridazinyl.

In one embodiment $A_1$ to $A_4$ are each independently selected from the group consisting of a bond, CR⁸, N, S and O, wherein $A_1$ to $A_4$ together with the atoms to which they are joined form a 5 to 6 membered aryl or heteroaryl.

In one embodiment $A_1$ to $A_4$ are each independently selected from the group consisting of a bond, CR⁸, N, S and O, wherein $A_1$ to $A_4$ together with the atoms to which they are joined form a 5-membered heteroaryl. For example, one of $A_1$ to $A_4$ is a bond, the ring formed by $A_1$ to $A_4$ is unsaturated, and in addition (a) one of $A_1$ to $A_4$ is nitrogen to form a pyrrole ring; (b) one of $A_1$ to $A_4$ is oxygen to form a furan ring; or (c) one of $A_1$ to $A_4$ is nitrogen and another of $A_1$ to $A_4$ is oxygen to form an oxazole or isoxazole ring.

In one embodiment $A_1$ to $A_4$ are each independently selected from the group consisting of CR⁸, N, S and O, wherein $A_1$ to $A_4$ together with the atoms to which they are joined form a 6-membered aryl or 6-membered heteroaryl. For example, the ring formed by $A_1$ to $A_4$ is unsaturated to form a phenyl ring. Alternatively, the ring formed by $A_1$ to $A_4$ is unsaturated, and in addition (a) one of $A_1$ to $A_4$ is nitrogen to form a pyridine ring; (b) two of $A_1$ to $A_4$ are nitrogen to form a diazine ring such as pyrazine, pyrimidine or pyridazine; or (c) one of $A_1$ to $A_4$ is nitrogen and another of $A_1$ to $A_4$ is oxygen to form an oxazine ring.

In one embodiment $A_1$ to $A_4$ are each independently selected from the group consisting of a C(R⁸)₂, C(R⁸)₂—C(R⁸)₂, NR⁸, S and O, wherein $A_1$ to $A_4$ together with the atoms to which they are joined form a 7-membered cycloalkyl or 7-membered heterocycloalkyl.

In one embodiment $A_1$ to $A_4$ are all CR⁸.

In one embodiment each R⁸ is independently selected from the group consisting of hydrogen, halogen, methyl, ethyl, methoxy, ethoxy, fluoromethyl and trifluoromethyl; or two R⁸ groups are joined via —OCH₂O— to form a dioxolane ring.

In one embodiment $A_1$ to $A_4$ together with the atoms to which they are joined form a phenyl, pyrimidinyl, isoxazolyl or thienyl ring. In one embodiment, $A_1$ to $A_4$ are all CH. In another embodiment $A_1$ and $A_3$ are N, and $A_2$ and $A_4$ are CH. In a further embodiment, $A_1$ and $A_4$ are N, and $A_2$ and $A_3$ are CH. In a further embodiment, $A_1$ is O, $A_2$ is N, $A_3$ is CH, and $A_4$ is a bond.

In one embodiment $A_1$ to $A_4$ together with the atoms to which they are joined form a phenyl, pyrimidinyl, isoxazolyl or thienyl ring optionally substituted with 1-4 R⁸. In a further embodiment the phenyl, pyrimidinyl, isoxazolyl or thienyl ring is optionally substituted with methyl, ethyl, methoxy or trifluoromethyl.

In one embodiment $A_1$ to $A_4$ together with the atoms to which they are joined form a phenyl ring optionally substituted with 1-4 R⁸.

In one embodiment one R⁸ is selected from the group consisting of hydrogen, fluoro, chloro, methyl, ethyl, methoxy, ethoxy, fluoromethyl and trifluoromethyl.

In one embodiment two R⁸ groups are joined via —OCH₂O— to form a 5-membered dioxolane ring.

In one embodiment of the present invention there is provided a compound of formula (I) wherein R¹ is methyl; R² is hydrogen or methyl; X is selected from the group consisting of OH, O—CH₃, O—C₂H₅, NH₂, NH(CH₃) and N(CH₃)₂; Y is selected from the group consisting of O, N-phenyl and N-3,5-difluoro-phenyl; Z is CH₂, CH₂—CH₂, (O)—CH₂, or O; $A_1$ to $A_4$ together with the atoms to which they are joined form a phenyl, pyrimidinyl, isoxazolyl or thienyl ring optionally substituted with 1-4 R⁸; and each R⁸ is independently selected from the group consisting of hydrogen, halogen, $C_1$-$C_4$ alkyl, $C_2$-$C_4$ alkenyl, $C_2$-$C_4$ alkynyl, $C_1$-$C_4$ alkoxy and $C_1$-$C_4$ haloalkyl; or two R⁸ groups are joined via —OCH₂O— to form a 5-membered dioxolane ring.

Compounds of formula (Ia) to (Ik) represent specific embodiments of the present invention:

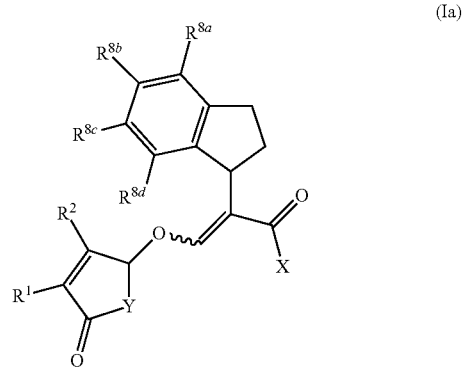

(Ia)

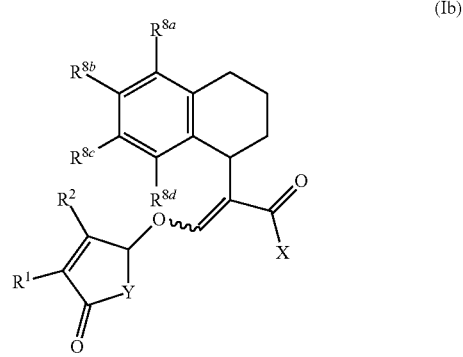

(Ib)

(Ic)
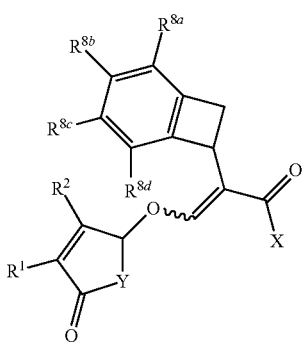

(Id)
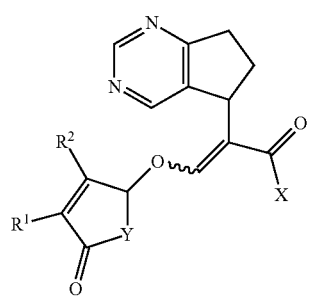

(Ie)
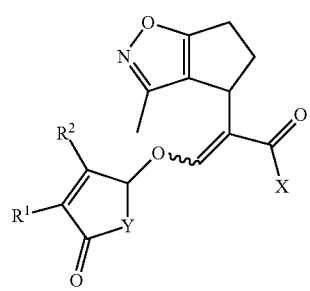

(If)
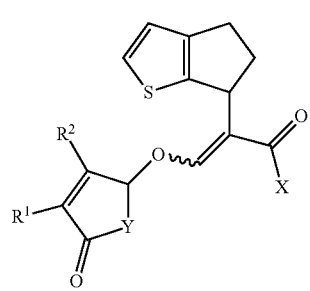

(Ig)
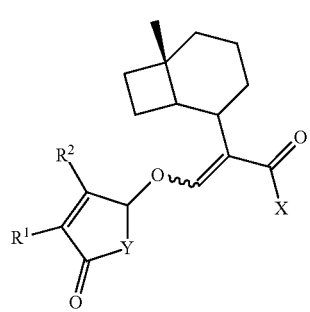

(Ih)
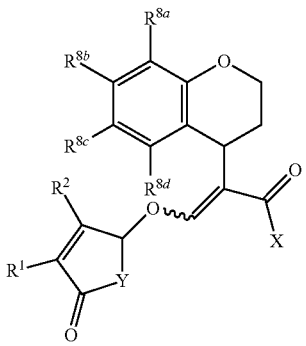

(Ii)
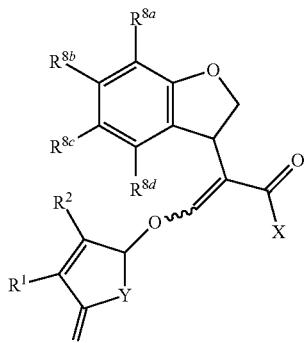

(Ij)
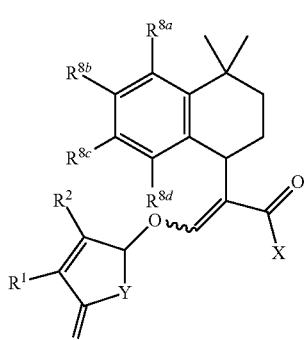

(Ik)
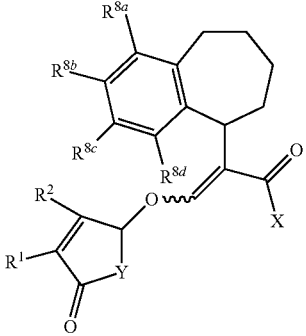

The definitions of $R^1$, $R^2$, X, $R^3$, $R^4$, $R^5$, Y, $R^6$, $R^7$ and $R^8$ are, in any combination, as described above.

According to the present invention there is provided a compound of formula (Ia), (Ib), (Ic), (Id), (Ie), (If), (Ig), (Ih), (Ii), (Ij) or (Ik) wherein $R^1$ is methyl and $R^2$ is hydrogen or methyl.

According to the present invention there is provided a compound of formula (Ia), (Ib), (Ic), (Id), (Ie), (If), (Ig), (Ih), (Ii), (Ij) or (Ik) wherein X is selected from the group consisting of OH, O—CH$_3$, O—C$_2$H$_5$, NH$_2$, NH(CH$_3$) and N(CH$_3$)$_2$.

According to the present invention there is provided a compound of formula (Ia), (Ib), (Ic), (Id), (Ie), (If), (Ig), (Ih), (Ii), (Ij) or (Ik) wherein Y is selected from the group consisting of O, N-phenyl and N-3,5-difluoro-phenyl.

According to the present invention there is provided a compound of formula (Ia), (Ib), (Ic), (Ig), (Ih), (Ii) or (Ik) wherein R$^{8a}$ to R$^{8d}$ are independently selected from the group consisting of hydrogen, halogen, C$_1$-C$_4$ alkyl, C$_2$-C$_4$ alkenyl, C$_2$-C$_4$ alkynyl, C$_1$-C$_4$ alkoxy and C$_1$-C$_4$ haloalkyl; or two R$^8$ groups are joined via —OCH$_2$O— to form a 5-membered dioxolane ring.

According to the present invention there is provided a compound of formula (Ia) wherein R$^1$ is methyl; R$^2$ is hydrogen or methyl; X is selected from the group consisting of OH, O—CH$_3$, O—C$_2$H$_5$, NH$_2$, NH(CH$_3$) and N(CH$_3$)$_2$; Y is selected from the group consisting of O, N-phenyl and N-3,5-difluoro-phenyl; and R$^{8a}$ to R$^{8d}$ are independently selected from the group consisting of hydrogen, halogen, C$_1$-C$_4$ alkyl, C$_2$-C$_4$ alkenyl, C$_2$-C$_4$ alkynyl, C$_1$-C$_4$ alkoxy and C$_1$-C$_4$ haloalkyl; or two R$^8$ groups are joined via —OCH$_2$O— to form a 5-membered dioxolane ring.

Compounds of formula (Im) to (Ip) represent further specific embodiments of the present invention:

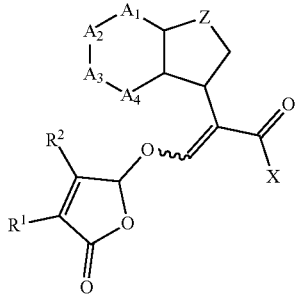
(Im)

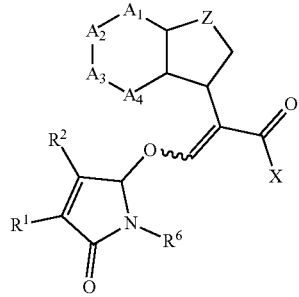
(In)

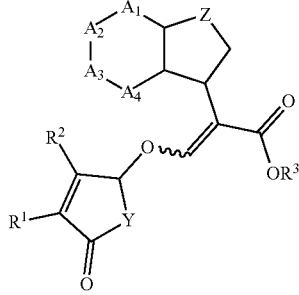
(Io)

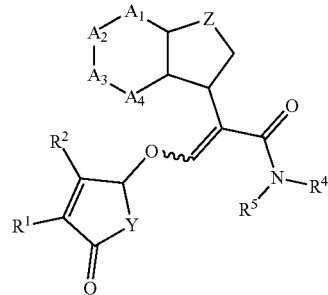
(Ip)

The definitions of R$^1$, R$^2$, X, R$^3$, R$^4$, R$^5$, Y, R$^6$, R$^7$, Z, A$_1$, A$_2$, A$_3$, A$_4$ and R$^8$ are, in any combination, as described above.

According to the present invention there is provided a compound of formula (Im), (In), (Io) or (Ip) wherein R$^1$ is methyl and R$^2$ is hydrogen or methyl.

According to the present invention there is provided a compound of formula (Im) or (Im) wherein X is selected from the group consisting of OH, O—CH$_3$, O—C$_2$H$_5$, NH$_2$, NH(CH$_3$) and N(CH$_3$)$_2$.

According to the present invention there is provided a compound of formula (Io) or (Ip) wherein Y is selected from the group consisting of O, N-phenyl and N-3,5-difluoro-phenyl.

According to the present invention there is provided a compound of formula (Im), (In), (Io) or (Ip) wherein A$_1$ to A$_4$ are all CH.

According to the present invention there is provided a compound of formula (Im), (In), (Io) or (Ip) wherein A$_1$ to A$_4$ together with the atoms to which they are joined form a phenyl, pyrimidinyl, isoxazolyl or thienyl ring optionally substituted with 1-4 R$^8$.

According to the present invention there is provided a compound of formula (Im), (In), (Io) or (Ip) wherein A$_1$ to A$_4$ together with the atoms to which they are joined form a phenyl, pyrimidinyl, isoxazolyl or thienyl ring optionally substituted with methyl, ethyl, methoxy or trifluoromethyl.

According to the present invention there is provided a compound of formula (Im), (In), (Io) or (Ip) wherein Z is a bond, CH$_2$, CH$_2$—CH$_2$, CH$_2$—CH$_2$—CH$_2$, (O)—CH$_2$, CH(CH$_3$)$_2$—CH$_2$, O or N.

Table 1 lists some specific compounds of the present invention.

Table 1: Compounds of formula (I) and the ring system is as shown in formula (Ia) to (Ik) R$^{8a}$-R$^{8d}$, R$^1$, R$^2$, X, R$^3$, R$^4$, R$^5$, Y and R$^6$ are as defined in the following table.

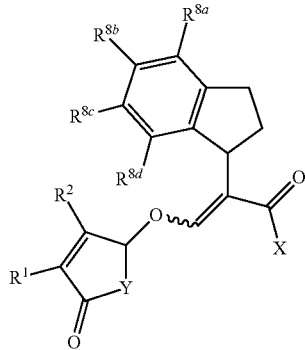
(Ia)

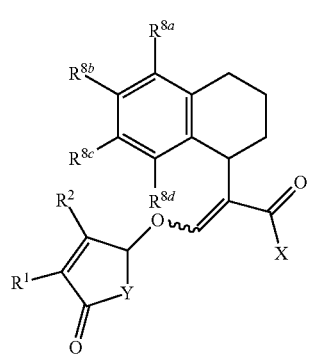
(Ib)
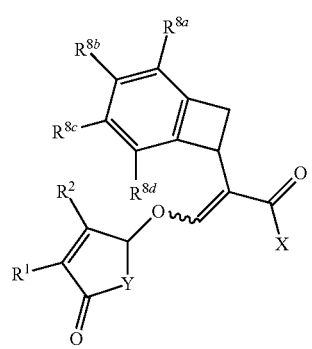
(Ic)
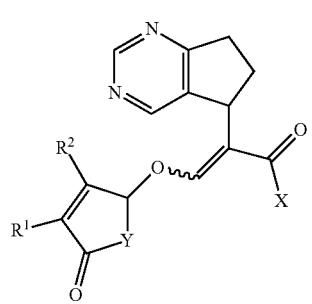
(Id)
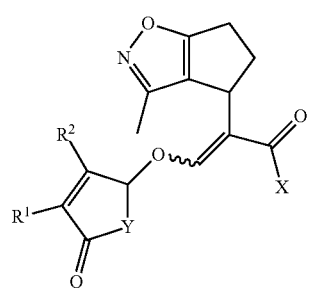
(Ie)
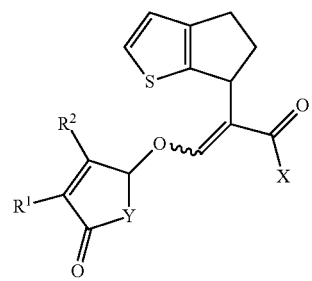
(If)
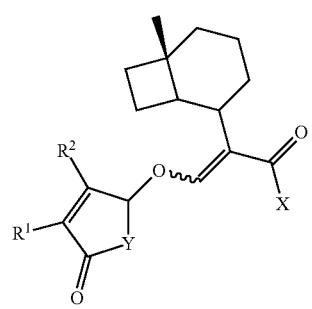
(Ig)
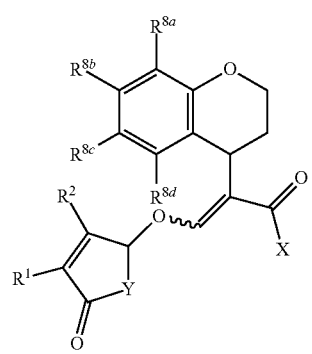
(Ih)
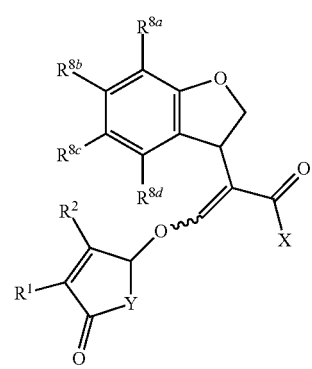
(Ii)

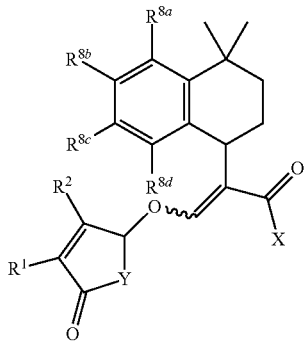

(Ij)

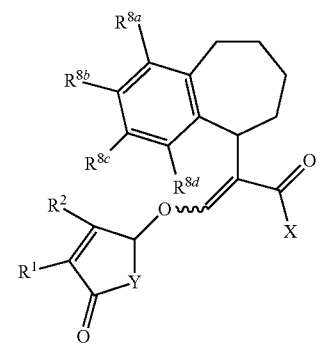

(Ik)

| Compound | Ring system | $R^{8a}$ | $R^{8b}$ | $R^{8c}$ | $R^{8d}$ | $R^1$ | $R^2$ | X | $R^3$ | $R^4$ | $R^5$ | Y | $R^6$ |
|---|---|---|---|---|---|---|---|---|---|---|---|---|---|
| I-1 | Ia | H | H | H | H | Me | H | O—$R^3$ | Et | — | — | O | — |
| I-2 | Ia | H | H | H | H | Me | Me | O—$R^3$ | Et | — | — | O | — |
| I-3 | Ia | H | H | H | H | Me | OMe | O—$R^3$ | Et | — | — | O | — |
| I-4 | Ia | H | H | H | H | Me | H | O—$R^3$ | Et | — | — | N—$R^6$ | Ph |
| I-5 | Ia | H | H | H | H | Me | Me | O—$R^3$ | Et | — | — | N—$R^6$ | Ph |
| I-6 | Ia | H | H | H | H | Me | OMe | O—$R^3$ | Et | — | — | N—$R^6$ | Ph |
| I-7 | Ia | H | H | H | H | Me | H | O—$R^3$ | Et | — | — | N—$R^6$ | 3,5-$(CF_3)_2$Ph |
| I-8 | Ia | H | H | H | H | Me | Me | O—$R^3$ | Et | — | — | N—$R^6$ | 3,5-$(CF_3)_2$Ph |
| I-9 | Ia | H | H | H | H | Me | OMe | O—$R^3$ | Et | — | — | N—$R^6$ | 3,5-$(CF_3)_2$Ph |
| I-10 | Ia | H | H | H | H | Me | H | O—$R^3$ | Me | — | — | O | — |
| I-11 | Ia | H | H | H | H | Me | Me | O—$R^3$ | Me | — | — | O | — |
| I-12 | Ia | H | H | H | H | Me | OMe | O—$R^3$ | Me | — | — | O | — |
| I-13 | Ia | H | H | H | H | Me | H | O—$R^3$ | Me | — | — | N—$R^6$ | Ph |
| I-14 | Ia | H | H | H | H | Me | Me | O—$R^3$ | Me | — | — | N—$R^6$ | Ph |
| I-15 | Ia | H | H | H | H | Me | OMe | O—$R^3$ | Me | — | — | N—$R^6$ | Ph |
| I-16 | Ia | H | H | H | H | Me | H | O—$R^3$ | Me | — | — | N—$R^6$ | 3,5-$(CF_3)_2$Ph |
| I-17 | Ia | H | H | H | H | Me | Me | O—$R^3$ | Me | — | — | N—$R^6$ | 3,5-$(CF_3)_2$Ph |
| I-18 | Ia | H | H | H | H | Me | OMe | O—$R^3$ | Me | — | — | N—$R^6$ | 3,5-$(CF_3)_2$Ph |
| I-19 | Ia | H | H | H | H | Me | H | O—$R^3$ | tBu | — | — | O | — |
| I-20 | Ia | H | H | H | H | Me | Me | O—$R^3$ | tBu | — | — | O | — |
| I-21 | Ia | H | H | H | H | Me | OMe | O—$R^3$ | tBu | — | — | O | — |
| I-22 | Ia | H | H | H | H | Me | H | O—$R^3$ | tBu | — | — | N—$R^6$ | Ph |
| I-23 | Ia | H | H | H | H | Me | Me | O—$R^3$ | tBu | — | — | N—$R^6$ | Ph |
| I-24 | Ia | H | H | H | H | Me | OMe | O—$R^3$ | tBu | — | — | N—$R^6$ | Ph |
| I-25 | Ia | H | H | H | H | Me | H | O—$R^3$ | tBu | — | — | N—$R^6$ | 3,5-$(CF_3)_2$Ph |
| I-26 | Ia | H | H | H | H | Me | Me | O—$R^3$ | tBu | — | — | N—$R^6$ | 3,5-$(CF_3)_2$Ph |
| I-27 | Ia | H | H | H | H | Me | OMe | O—$R^3$ | tBu | — | — | N—$R^6$ | 3,5-$(CF_3)_2$Ph |
| I-28 | Ia | H | H | H | H | Me | H | O—$R^3$ | H | — | — | O | — |
| I-29 | Ia | H | H | H | H | Me | Me | O—$R^3$ | H | — | — | O | — |
| I-30 | Ia | H | H | H | H | Me | OMe | O—$R^3$ | H | — | — | O | — |
| I-31 | Ia | H | H | H | H | Me | H | O—$R^3$ | H | — | — | N—$R^6$ | Ph |
| I-32 | Ia | H | H | H | H | Me | Me | O—$R^3$ | H | — | — | N—$R^6$ | Ph |
| I-33 | Ia | H | H | H | H | Me | OMe | O—$R^3$ | H | — | — | N—$R^6$ | Ph |
| I-34 | Ia | H | H | H | H | Me | H | O—$R^3$ | H | — | — | N—$R^6$ | 3,5-$(CF_3)_2$Ph |
| I-35 | Ia | H | H | H | H | Me | Me | O—$R^3$ | H | — | — | N—$R^6$ | 3,5-$(CF_3)_2$Ph |
| I-36 | Ia | H | H | H | H | Me | OMe | O—$R^3$ | H | — | — | N—$R^6$ | 3,5-$(CF_3)_2$Ph |
| I-37 | Ia | H | H | H | H | Me | H | N—$R^4R^5$ | — | Me | H | O | — |
| I-38 | Ia | H | H | H | H | Me | Me | N—$R^4R^5$ | — | Me | H | O | — |
| I-39 | Ia | H | H | H | H | Me | OMe | N—$R^4R^5$ | — | Me | H | O | — |
| I-40 | Ia | H | H | H | H | Me | H | N—$R^4R^5$ | — | Me | Me | O | — |
| I-41 | Ia | H | H | H | H | Me | Me | N—$R^4R^5$ | — | Me | Me | O | — |
| I-42 | Ia | H | H | H | H | Me | OMe | N—$R^4R^5$ | — | Me | Me | O | — |
| I-43 | Ia | H | H | H | H | Me | H | N—$R^4R^5$ | — | Heterocyclopentyl | | O | — |
| I-44 | Ia | H | H | H | H | Me | Me | N—$R^4R^5$ | — | Heterocyclopentyl | | O | — |
| I-45 | Ia | H | H | H | H | Me | OMe | N—$R^4R^5$ | — | Heterocyclopentyl | | O | — |
| I-46 | Ia | H | H | H | H | Me | H | N—$R^4R^5$ | — | Me | H | N—$R^6$ | Ph |
| I-47 | Ia | H | H | H | H | Me | Me | N—$R^4R^5$ | — | Me | H | N—$R^6$ | Ph |
| I-48 | Ia | H | H | H | H | Me | OMe | N—$R^4R^5$ | — | Me | H | N—$R^6$ | Ph |
| I-49 | Ia | H | H | H | H | Me | H | N—$R^4R^5$ | — | Me | Me | N—$R^6$ | Ph |
| I-50 | Ia | H | H | H | H | Me | Me | N—$R^4R^5$ | — | Me | Me | N—$R^6$ | Ph |
| I-51 | Ia | H | H | H | H | Me | OMe | N—$R^4R^5$ | — | Me | Me | N—$R^6$ | Ph |
| I-52 | Ia | H | H | H | H | Me | H | N—$R^4R^5$ | — | Heterocyclopentyl | | N—$R^6$ | Ph |
| I-53 | Ia | H | H | H | H | Me | Me | N—$R^4R^5$ | — | Heterocyclopentyl | | N—$R^6$ | Ph |
| I-54 | Ia | H | H | H | H | Me | OMe | N—$R^4R^5$ | — | Heterocyclopentyl | | N—$R^6$ | Ph |
| I-55 | Ia | H | H | H | H | Me | H | N—$R^4R^5$ | — | Me | H | N—$R^6$ | 3,5-$(CF_3)_2$Ph |
| I-56 | Ia | H | H | H | H | Me | Me | N—$R^4R^5$ | — | Me | H | N—$R^6$ | 3,5-$(CF_3)_2$Ph |
| I-57 | Ia | H | H | H | H | Me | OMe | N—$R^4R^5$ | — | Me | H | N—$R^6$ | 3,5-$(CF_3)_2$Ph |

-continued

| Compound | Ring system | $R^{8a}$ | $R^{8b}$ | $R^{8c}$ | $R^{8d}$ | $R^1$ | $R^2$ | X | $R^3$ | $R^4$ | $R^5$ | Y | $R^6$ |
|---|---|---|---|---|---|---|---|---|---|---|---|---|---|
| I-58 | Ia | H | H | H | H | Me | H | N—$R^4R^5$ | — | Me | Me | N—$R^6$ | 3,5-$(CF_3)_2$Ph |
| I-59 | Ia | H | H | H | H | Me | Me | N—$R^4R^5$ | — | Me | Me | N—$R^6$ | 3,5-$(CF_3)_2$Ph |
| I-60 | Ia | H | H | H | H | Me | OMe | N—$R^4R^5$ | — | Me | Me | N—$R^6$ | 3,5-$(CF_3)_2$Ph |
| I-61 | Ia | H | H | H | H | Me | H | N—$R^4R^5$ | — | Heterocyclopentyl | | N—$R^6$ | 3,5-$(CF_3)_2$Ph |
| I-62 | Ia | H | H | H | H | Me | Me | N—$R^4R^5$ | — | Heterocyclopentyl | | N—$R^6$ | 3,5-$(CF_3)_2$Ph |
| I-63 | Ia | H | H | H | H | Me | OMe | N—$R^4R^5$ | — | Heterocyclopentyl | | N—$R^6$ | 3,5-$(CF_3)_2$Ph |
| I-64 | Ia | H | OMe | OMe | H | Me | H | O—$R^3$ | Et | — | — | O | — |
| I-65 | Ia | H | OMe | OMe | H | Me | Me | O—$R^3$ | Et | — | — | O | — |
| I-66 | Ia | H | —OCH$_2$O— | | H | Me | H | O—$R^3$ | Et | — | — | O | — |
| I-67 | Ia | H | —OCH$_2$O— | | H | Me | Me | O—$R^3$ | Et | — | — | O | — |
| I-68 | Ia | Me | H | H | H | Me | H | O—$R^3$ | Et | — | — | O | — |
| I-69 | Ia | Me | H | H | H | Me | Me | O—$R^3$ | Et | — | — | O | — |
| I-70 | Ia | CF$_3$ | H | H | H | Me | H | O—$R^3$ | Et | — | — | O | — |
| I-71 | Ia | CF$_3$ | H | H | H | Me | Me | O—$R^3$ | Et | — | — | O | — |
| I-72 | Ia | H | H | CF$_3$ | H | Me | H | O—$R^3$ | Et | — | — | O | — |
| I-73 | Ia | H | H | CF$_3$ | H | Me | Me | O—$R^3$ | Et | — | — | O | — |
| I-74 | Ib | H | H | H | H | Me | H | O—$R^3$ | Et | — | — | O | — |
| I-75 | Ib | H | H | H | H | Me | Me | O—$R^3$ | Et | — | — | O | — |
| I-76 | Ic | H | H | H | H | Me | H | O—$R^3$ | Et | — | — | O | — |
| I-77 | Ic | H | H | H | H | Me | Me | O—$R^3$ | Et | — | — | O | — |
| I-78 | Id | — | — | — | — | Me | H | O—$R^3$ | Et | — | — | O | — |
| I-79 | Id | — | — | — | — | Me | Me | O—$R^3$ | Et | — | — | O | — |
| I-80 | Id | — | — | — | — | Me | H | O—$R^3$ | Et | — | — | N—$R^6$ | 3,5-$(CF_3)_2$Ph |
| I-81 | Id | — | — | — | — | Me | H | N—$R^4R^5$ | — | Me | H | N—$R^6$ | 3,5-$(CF_3)_2$Ph |
| I-80 | Ie | — | — | — | — | Me | H | O—$R^3$ | Et | — | — | O | — |
| I-81 | Ie | — | — | — | — | Me | Me | O—$R^3$ | Et | — | — | O | — |
| I-82 | Ie | — | — | — | — | Me | H | O—$R^3$ | Et | — | — | N—$R^6$ | 3,5-$(CF_3)_2$Ph |
| I-83 | Ie | — | — | — | — | Me | H | N—$R^4R^5$ | — | Me | H | N—$R^6$ | 3,5-$(CF_3)_2$Ph |
| I-82 | If | — | — | — | — | Me | H | O—$R^3$ | Et | — | — | O | — |
| I-83 | If | — | — | — | — | Me | Me | O—$R^3$ | Et | — | — | O | — |
| I-84 | If | — | — | — | — | Me | Me | O—$R^3$ | Et | — | — | N—$R^6$ | 3,5-$(CF_3)_2$Ph |
| I-85 | If | — | — | — | — | Me | H | N—$R^4R^5$ | — | Me | H | N—$R^6$ | 3,5-$(CF_3)_2$Ph |
| I-86 | Ig | — | — | — | — | Me | H | O—$R^3$ | Et | — | — | O | — |
| I-87 | Ig | — | — | — | — | Me | Me | O—$R^3$ | Et | — | — | O | — |
| I-88 | Ig | — | — | — | — | Me | H | O—$R^3$ | Et | — | — | N—$R^6$ | 3,5-$(CF_3)_2$Ph |
| I-89 | Ig | — | — | — | — | Me | H | N—$R^4R^5$ | — | Me | H | N—$R^6$ | 3,5-$(CF_3)_2$Ph |
| I-90 | Ih | H | H | H | H | Me | H | O—$R^3$ | Et | — | — | O | — |
| I-91 | Ih | H | H | H | H | Me | Me | O—$R^3$ | Et | — | — | O | — |
| I-92 | Ih | H | H | H | H | Me | H | O—$R^3$ | Et | — | — | N—$R^6$ | 3,5-$(CF_3)_2$Ph |
| I-93 | Ih | H | H | H | H | Me | H | N—$R^4R^5$ | — | Me | H | N—$R^6$ | 3,5-$(CF_3)_2$Ph |
| I-94 | Ii | H | H | H | H | Me | H | O—$R^3$ | Et | — | — | O | — |
| I-95 | Ii | H | H | H | H | Me | Me | O—$R^3$ | Et | — | — | O | — |
| I-96 | Ii | H | H | H | H | Me | H | O—$R^3$ | Et | — | — | N—$R^6$ | 3,5-$(CF_3)_2$Ph |
| I-97 | Ii | H | H | H | H | Me | H | N—$R^4R^5$ | — | Me | H | N—$R^6$ | 3,5-$(CF_3)_2$Ph |
| I-98 | Ij | H | H | H | H | Me | H | O—$R^3$ | Et | — | — | O | — |
| I-99 | Ij | H | H | H | H | Me | Me | O—$R^3$ | Et | — | — | O | — |
| I-100 | Ij | H | H | H | H | Me | H | O—$R^3$ | Et | — | — | N—$R^6$ | 3,5-$(CF_3)_2$Ph |
| I-101 | Ij | H | H | H | H | Me | H | N—$R^4R^5$ | — | Me | H | N—$R^6$ | 3,5-$(CF_3)_2$Ph |
| I-102 | Ik | H | H | H | H | Me | H | O—$R^3$ | Et | — | — | O | — |
| I-103 | Ik | H | H | H | H | Me | Me | O—$R^3$ | Et | — | — | O | — |
| I-104 | Ik | H | H | H | H | Me | H | O—$R^3$ | Et | — | — | N—$R^6$ | 3,5-$(CF_3)_2$Ph |
| I-105 | Ik | H | H | H | H | Me | H | N—$R^4R^5$ | — | Me | H | N—$R^6$ | 3,5-$(CF_3)_2$Ph |

Me = methyl;
Et = ethyl;
tBu = tert-butyl;
Ph = phenyl

In one embodiment, the compounds of the present invention are applied in combination with an agriculturally acceptable adjuvant. In particular, there is provided a composition comprising a compound of the present invention and an agriculturally acceptable adjuvant. There may also be mentioned an agrochemical composition comprising a compound of the present invention.

The present invention provides a method of improving the tolerance of a plant to abiotic stress, wherein the method comprises applying to the plant, plant part, plant propagation material, or plant growing locus a compound, composition or mixture according to the present invention.

The present invention provides a method for regulating or improving the growth of a plant, wherein the method comprises applying to the plant, plant part, plant propagation material, or plant growing locus a compound, composition or mixture according to the present invention. In one embodiment, plant growth is regulated or improved when the plant is subject to abiotic stress conditions.

The present invention also provides a method for improving the hydrolytic conductivity of a plant, wherein the method comprises applying to the plant, plant part, plant propagation material, or plant growing locus a compound, composition or mixture according to the present invention.

The present invention also provides a method for promoting seed germination of a plant, comprising applying to the seed, or a locus containing seeds, a compound, composition or mixture according to the present invention.

The present invention also provides a method for controlling weeds comprising applying to a locus containing weed seeds a seed germination promoting amount of a compound, composition or mixture according to the present invention, allowing the seeds to germinate, and then applying to the locus a post-emergence herbicide. The present invention also provides a method for safening a plant against phytotoxic effects of chemicals, comprising applying to the plant, plant part, plant propagation material, or plant growing locus a compound, composition or mixture according to the present invention.

Suitably the compound or composition is applied in an amount sufficient to elicit the desired response.

According to the present invention, "regulating or improving the growth of a crop" means an improvement in plant vigour, an improvement in plant quality, improved tolerance to stress factors, and/or improved input use efficiency.

An 'improvement in plant vigour' means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased root nodulation, increased shoot growth, increased tillering, stronger tillers, more productive tillers, increased or improved plant stand, less plant verse (lodging), an increase and/or improvement in plant height, an increase in plant weight (fresh or dry), bigger leaf blades, greener leaf colour, increased pigment content, increased photosynthetic activity, earlier flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant, increased levels of amino acids in storage tissues and/or less inputs needed (e.g. less fertiliser, water and/or labour needed). A plant with improved vigour may have an increase in any of the aforementioned traits or any combination or two or more of the aforementioned traits.

An 'improvement in plant quality' means that certain traits are improved qualitatively or quantitatively when compared with the same trait in a control plant which has been grown under the same conditions in the absence of the method of the invention. Such traits include, but are not limited to, improved visual appearance of the plant, reduced ethylene (reduced production and/or inhibition of reception), improved quality of harvested material, e.g. seeds, fruits, leaves, vegetables (such improved quality may manifest as improved visual appearance of the harvested material), improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds), more homogenous crop development (e.g. synchronised germination, flowering and/or fruiting of plants), and/or improved seed quality (e.g. for use in following seasons). A plant with improved quality may have an increase in any of the aforementioned traits or any combination or two or more of the aforementioned traits.

An 'improved tolerance to stress factors' means that certain traits are improved qualitatively or quantitatively when compared with the same trait in a control plant which has been grown under the same conditions in the absence of the method of the invention. Such traits include, but are not limited to, an increased tolerance and/or resistance to biotic and/or abiotic stress factors, and in particular abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. In particular, the compounds or compositions of the present invention are useful to improve tolerance to drought stress.

An 'improved input use efficiency' means that the plants are able to grow more effectively using given levels of inputs compared to the grown of control plants which are grown under the same conditions in the absence of the method of the invention. In particular, the inputs include, but are not limited to fertiliser (such as nitrogen, phosphorous, potassium, micronutrients), light and water. A plant with improved input use efficiency may have an improved use of any of the aforementioned inputs or any combination of two or more of the aforementioned inputs.

Other effects of regulating or improving the growth of a crop include a decrease in plant height, or reduction in tillering, which are beneficial features in crops or conditions where it is desirable to have less biomass and fewer tillers.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield, starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

In one aspect of the present invention, crop enhancements are made in the substantial absence of pressure from pests and/or diseases and/or abiotic stress. In a further aspect of the present invention, improvements in plant vigour, stress tolerance, quality and/or yield are made in the substantial absence of pressure from pests and/or diseases. For example pests and/or diseases may be controlled by a pesticidal treatment that is applied prior to, or at the same time as, the method of the present invention. In a still further aspect of the present invention, improvements in plant vigour, stress tolerance, quality and/or yield are made in the absence of pest and/or disease pressure. In a further embodiment, improvements in plant vigour, quality and/or yield are made in the absence, or substantial absence, of abiotic stress.

The compounds of the present invention can be used alone, but are generally formulated into compositions using formulation adjuvants, such as carriers, solvents and surface-active agents (SFAs). Thus, the present invention further provides a composition comprising a compound of the present invention and an agriculturally acceptable formulation adjuvant. There is also provided a composition consisting essentially of a compound of the present invention and an agriculturally acceptable formulation adjuvant. There is also provided a composition consisting of a compound of the present invention and an agriculturally acceptable formulation adjuvant.

The present invention further provides a crop yield enhancing composition comprising a compound of the present invention and an agriculturally acceptable formulation adjuvant. There is also provided a crop yield enhancing composition consisting essentially of a compound of the present invention and an agriculturally acceptable formulation adjuvant. There is also provided a crop yield enhancing composition consisting of a compound of the present invention and an agriculturally acceptable formulation adjuvant.

The present invention further provides a plant growth regulator composition comprising a compound of the present invention and an agriculturally acceptable formulation adjuvant. There is also provided a plant growth regulator composition consisting essentially of a compound of the present invention and an agriculturally acceptable formulation adjuvant. There is also provided a plant growth regulator composition consisting of a compound of the present invention and an agriculturally acceptable formulation adjuvant.

The present invention further provides a plant abiotic stress management composition comprising a compound of the present invention and an agriculturally acceptable formulation adjuvant. There is also provided a plant abiotic stress management composition consisting essentially of a compound of the present invention and an agriculturally acceptable formulation adjuvant. There is also provided a plant abiotic stress management composition consisting of a compound of the present invention and an agriculturally acceptable formulation adjuvant.

The present invention further provides a seed germination promoting composition comprising a compound of the present invention and an agriculturally acceptable formulation adjuvant. There is also provided a seed germination promoting composition consisting essentially of a compound of the present invention and an agriculturally acceptable formulation adjuvant. There is also provided a seed germination promoting composition consisting of a compound of the present invention and an agriculturally acceptable formulation adjuvant.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of the present invention and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultralow volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of the present invention.

Dustable powders (DP) may be prepared by mixing a compound of the present invention with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of the present invention with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of the present invention with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of the present invention and one or more powdered solid diluents or carriers, or from preformed blank granules by absorbing a compound of the present invention (or a solution thereof, in a suitable agent) in a porous granular material (such as pumice, attapulgite clays, fuller's earth, kieselguhr, diatomaceous earths or ground corn cobs) or by adsorbing a compound of the present invention (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of the present invention in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of the present invention in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of the present invention either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of the present invention is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of the present invention. SCs may be prepared by ball or bead milling the solid compound of the present invention in a suitable medium, optionally with one or more dispersing agents, to produce a fine particle suspension of the compound. One or more wetting agents may be included in the composition and a suspending agent may be included to reduce the rate at which the particles settle. Alternatively, a compound of the present invention may be dry milled and added to water, containing agents hereinbefore described, to produce the desired end product.

Aerosol formulations comprise a compound of the present invention and a suitable propellant (for example n-butane). A compound of the present invention may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of the present invention and, optionally, a carrier or diluent therefor. The polymeric shell may be produced by either an interfacial polycondensation reaction or by a coacervation procedure. The compositions may provide for controlled release of the compound of the present invention and they may be used for seed treatment. A compound of the present invention may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of the present invention. Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of the present invention).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The compound or composition of the present invention may be applied to a plant, part of the plant, plant organ, plant propagation material or a plant growing locus.

The term "plants" refers to all physical parts of a plant, including seeds, seedlings, saplings, roots, tubers, stems, stalks, foliage, and fruits.

The term "locus" as used herein means fields in or on which plants are growing, or where seeds of cultivated plants are sown, or where seed will be placed into the soil. It includes soil, seeds, and seedlings, as well as established vegetation.

The term "plant propagation material" denotes all generative parts of a plant, for example seeds or vegetative parts of plants such as cuttings and tubers. It includes seeds in the strict sense, as well as roots, fruits, tubers, bulbs, rhizomes, and parts of plants.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound or composition of the present invention may be applied pre-emergence or post-emergence. Suitably, where the composition is used to regulate the growth of crop plants or enhance the tolerance to abiotic stress, it may be applied post-emergence of the crop. Where the composition is used to promote the germination of seeds, it is applied pre-emergence.

The present invention envisages application of the compounds or compositions of the invention to plant propagation material prior to, during, or after planting, or any combination of these.

Although active ingredients can be applied to plant propagation material in any physiological state, a common approach is to use seeds in a sufficiently durable state to incur no damage during the treatment process. Typically, seed would have been harvested from the field; removed from the plant; and separated from any cob, stalk, outer husk, and surrounding pulp or other non-seed plant material. Seed would preferably also be biologically stable to the extent that treatment would not cause biological damage to the seed. It is believed that treatment can be applied to seed at any time between seed harvest and sowing of seed including during the sowing process.

Methods for applying or treating active ingredients on to plant propagation material or to the locus of planting are known in the art and include dressing, coating, pelleting and soaking as well as nursery tray application, in furrow application, soil drenching, soil injection, drip irrigation, application through sprinklers or central pivot, or incorporation into soil (broad cast or in band). Alternatively or in addition active ingredients may be applied on a suitable substrate sown together with the plant propagation material.

The rates of application of compounds of the present invention may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of the present invention according to the invention are generally applied at a rate of from 1 to 2000 g/ha, especially from 5 to 1000 g/ha. For seed treatment the rate of application is generally between 0.0005 and 150 g per 100 kg of seed.

The compounds and compositions of the present invention may be applied to dicotyledonous or monocotyledonous crops. Crops of useful plants in which the composition according to the invention can be used include perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

Crops are to be understood as being those which are naturally occurring, obtained by conventional methods of breeding, or obtained by genetic engineering. They include crops which contain so-called output traits (e.g. improved storage stability, higher nutritional value and improved flavour).

Crops are to be understood as also including those crops which have been rendered tolerant to herbicides like bromoxynil or classes of herbicides such as ALS-, EPSPS-, GS-, HPPD- and PPO-inhibitors. An example of a crop that has been rendered tolerant to imidazolinones, e.g. imazamox, by conventional methods of breeding is Clearfield® summer canola. Examples of crops that have been rendered tolerant to herbicides by genetic engineering methods include e.g. glyphosate- and glufosinate-resistant maize varieties commercially available under the trade names RoundupReady®, Herculex I® and LibertyLink®. Crops are also to be understood as being those which naturally are or have been rendered resistant to harmful insects. This includes plants transformed by the use of recombinant DNA techniques, for example, to be capable of synthesising one or more selectively acting toxins, such as are known, for example, from toxin-producing bacteria. Examples of toxins which can be expressed include δ-endotoxins, vegetative insecticidal proteins (Vip), insecticidal proteins of bacteria colonising nematodes, and toxins produced by scorpions, arachnids, wasps and fungi.

An example of a crop that has been modified to express the *Bacillus thuringiensis* toxin is the Bt maize KnockOut® (Syngenta Seeds). An example of a crop comprising more than one gene that codes for insecticidal resistance and thus expresses more than one toxin is VipCot® (Syngenta Seeds). Crops or seed material thereof can also be resistant to multiple types of pests (so-called stacked transgenic events when created by genetic modification). For example, a plant can have the ability to express an insecticidal protein while at the same time being herbicide tolerant, for example Herculex I® (Dow AgroSciences, Pioneer Hi-Bred International).

Compounds of the present invention may also be used to promote the germination of seeds of non-crop plants, for example as part of an integrated weed control program.

Normally, in the management of a crop a grower would use one or more other agronomic chemicals or biologicals in addition to the compound or composition of the present invention. There is also provided a mixture comprising a compound or composition of the present invention, and a further active ingredient.

Examples of agronomic chemicals or biologicals include pesticides, such as acaricides, bactericides, fungicides, herbicides, insecticides, nematicides, plant growth regulators, crop enhancing agents, safeners as well as plant nutrients and plant fertilizers. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops. The combination may also encompass specific plant traits incorporated into the plant using any means, for example conventional breeding or genetic modification.

The present invention also provides the use of a compound of formula (I), (Ia), (Ib), (Ic), (Id), (Ie), (If), (Ig), (Ih), (Ii), (Ij), (Ik), (Im), (In), (Io) or (Ip), or a composition comprising a compound according to formula (I), (Ia), (Ib), (Ic), (Id), (Ie), (If), (Ig), (Ih), (Ii), (Ij), (Ik), (Im), (In), (Io) or (Ip) and an agriculturally acceptable formulation adjuvant, for improving the tolerance of a plant to abiotic stress, regulating or improving the growth of a plant, promoting seed germination and/or safening a plant against phytotoxic effects of chemicals.

There is also provided the use of a compound, composition or mixture of the present invention, for improving the tolerance of a plant to abiotic stress, regulating or improving the growth of a plant, promoting seed germination and/or safening a plant against phytotoxic effects of chemicals.

The compounds of the invention may be made by the following methods.

Reaction Scheme 1

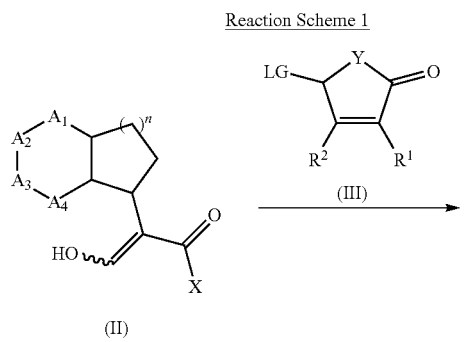

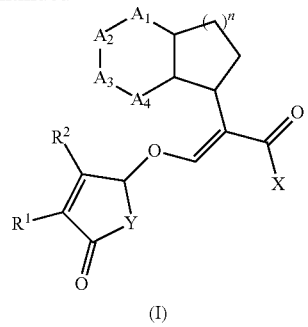

Compounds of formula (I) may be prepared from compounds of formula (II) by reaction with a compound of formula (II) and compound (III) wherein Lg is a leaving group, in the presence of a base such potassium tert-butylate or sodium tert-butylate, in the presence or not of a crown ether to activate the base. The reaction can also be carried out in the presence of a catalytic or stoichiometric amount of iodine salt, such as potassium iodide or tetrabutyl ammonium iodide. Compounds of formula (I) can be prepared by a method similar to what is described in WO 12/080115 and GB 1 591 374.

Reaction Scheme 2

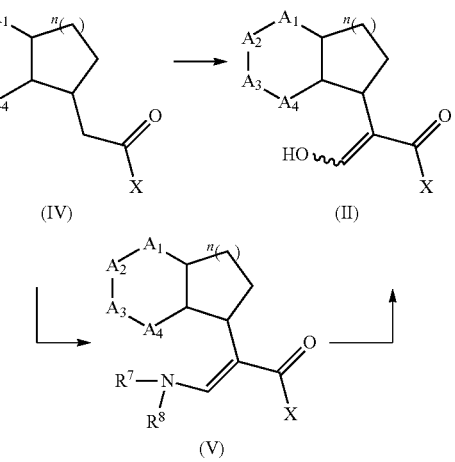

Compound of formula (II) may be prepared from a compound of formula (IV) via reaction with a formic ester derivative such as the methyl formate in presence of base such as lithium diisopropylamide, sodium hydride, potassium tert-butylate or sodium tert-butylate or a Lewis acid such as $TiCl_4$ in combination of a base such as triethylamine. Alternatively, compounds of formula (II) may be prepared from a compound of formula (V) via hydrolysis with an acid such as hydrogen chloride. Compounds of formula (V) may be prepared from a compound of formula (IV) via reaction with Bredereck's reagent (tert-butoxybis(dimethylamino) methane) wherein $R^7/R^8$ is a methyl or analogue. Compounds of formula (II) can be prepared by a method similar to what is described in WO 12/080115 and GB 1 591 374.

Reaction Scheme 3

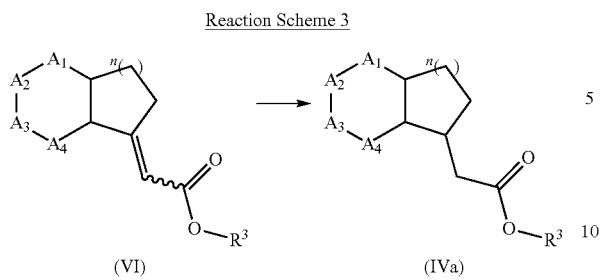

Compound of formula (IVa) may be prepared form compound of formula (VI) or any related isomers via hydrogenation reaction using hydrogen gas together with a metal source such as palladium, rhodium or platinum, optionally in a presence of a phosphine ligand.

Reaction Scheme 4

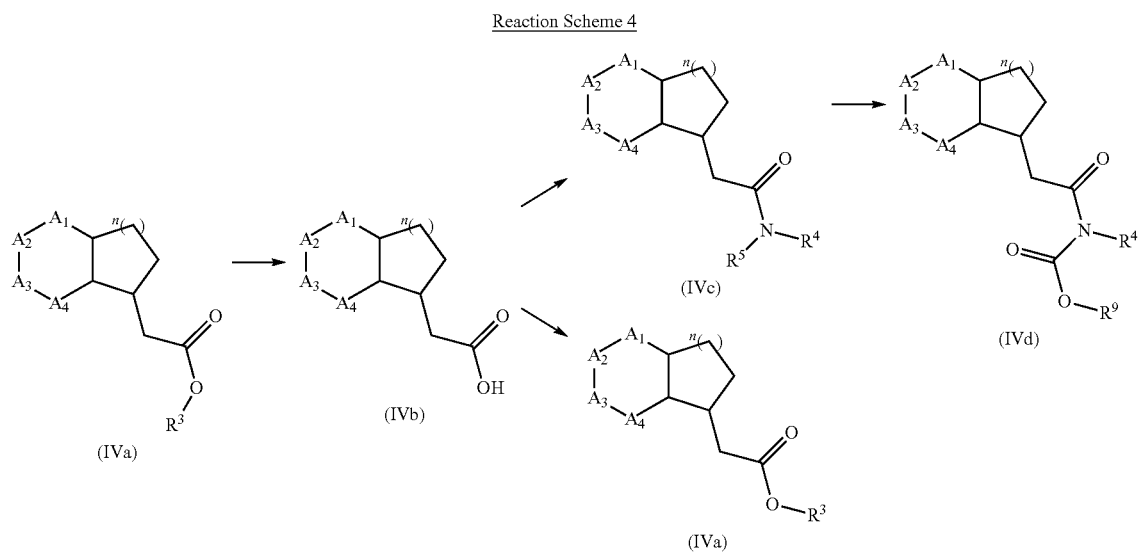

Alternatively, compound of formula (IVa) may be prepared form compound of formula (IVb) using a specific alcoholic solvent such as methanol or tert-butanol and an acid such as sulfuric or hydrochloric acid. Compound of formula (IVc) may be prepared from compound of formula (IVb) using a chlorinating agent such as thionyl chloride ($SOCl_2$) or oxalyl chloride ($(COCl)_2$) and a specific primary or secondary amine ($R^4R^5NH$). Alternatively, compound of formula (IVc) may be prepared from compound of formula (VIb) using dicyclohexylcarbodiimide (DCC), diisopropyl-carbodiimide (DIC) or N-(3-Dimethylaminopropyl)-N'-ethylcarbodiimide (EDAC.HCl) together with an additive such as 1-Hydroxybenzotriazole (HOBt), Hydroxy-3,4-dihydro-4-oxo-1,2,3-benzotriazine (HODhbt), N-Hydroxysuccinimide (HOSu), 1-Hydroxy-7-aza-1H-benzotriazole (HOAt) or 4-(N,N-Dimethylamino)pyridine (DMAP). If $R^5$ is hydrogen, compound of formula (IVc) can be transformed into compound of formula (IVd), wherein $R^6$ is a $C_1$-$C_4$ linear or substituted alkyl group such as tertbutyl, using an anhydride such as di-tert-butyl dicarbonate, a base such as trimethylamine ($Et_3N$) and a nucleophile such as 4-(dimethylamino)pyridine (DMAP). Compound of formula (IVb) may be prepared from compound of formula (IVa) using an aqueous solution of a base such as potassium, sodium or lithium hydroxide together with a miscible organic solvent such as tetrahydrofurane, methanol or dioxane.

Reaction Scheme 5

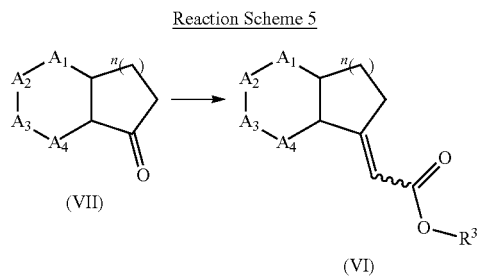

Compounds of formula (VI) may be prepared from a compound of formula (VII) using phosphonate such as ethyl 2-diethoxyphosphorylacetate in presence of a base such as sodium hydride in an organic solvent such as tetrahydrofuran. Alternatively, compound of formula (VI) can be prepared from compound of formula (VI) using ethyl 2-bromoacetate and zinc in an organic solvent such as tetrahydrofuran.

Reaction Scheme 6

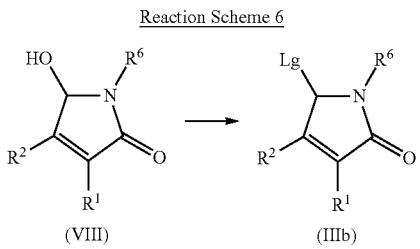

Compounds of formula (IIIb) wherein Lg is a leaving group, such as halogen, may be prepared from compound of formula (VIII) by reaction with a chlorinating agent such as thionyl chloride, phosgene or 1-chloro-N,N,2-trimethyl-1-propenylamine or a brominating agent such as $PBr_3$ or thionyl bromide, in the presence or not of a base such as pyridine. Compounds of formula (III) wherein Lg is a leaving group such alkylsulfonyl or aryl sulfonyl may be prepared from compound of formula (VIII) by reaction with the corresponding alkylsulfonyl chloride or aryl sulfonyl chloride in the presence of a base such as triethyl amine or pyridine. Compounds of formula (III) can be prepared by a method similar to what is described in WO2015/128321.

Reaction Scheme 7

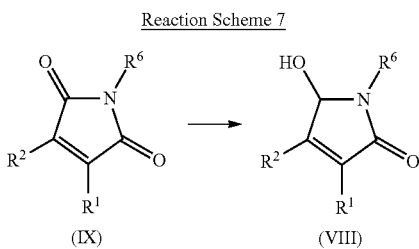

A compound of Formula (VIII) may be prepared from compound of Formula (IX) by reaction with a reducing agent such as diisopropylaluminium hydride, sodium cyanoborohydride or sodium borohydride, optionally in the presence of a Lewis acid such as cerium trichloride. Compounds of formula (VIII) can be prepared by a method similar to what is described in WO2015/128321.

Reaction Scheme 8

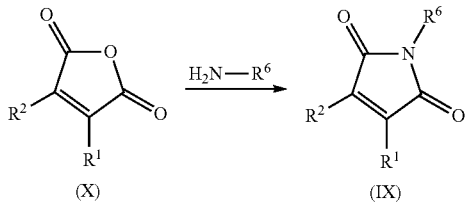

A compound of formula (IX) may be prepared from a known and commercially available compound of formula (X) by reaction with an amine of formula $R^9NH_2$ or its corresponding salt by heating in an alcoholic solvent or acetic acid. Compounds of formula (IX) can be prepared by a method similar to what is described in WO2015/128321.

The Examples which follow serve to illustrate the invention.

COMPOUND SYNTHESIS AND CHARACTERIZATION

The following abbreviations are used throughout this section: s=singlet; bs=broad singlet; d=doublet; dd=double doublet; dt=double triplet; bd=broad doublet; t=triplet; td=triplet doublet; bt=broad triplet; tt=triple triplet; q=quartet; m=multiplet; Me=methyl; Et=ethyl; Pr=propyl; Bu=butyl; DME=1,2-dimethoxyethane; THF=tetrahydrofuran; M.p.=melting point; RT=retention time, MH$^+$=molecular cation (i.e. measured molecular weight).

The following HPLC-MS methods were used for the analysis of the compounds:

Method A:

Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 µm, 30×2.1 mm, Temp: 60° C., flow rate 0.85 mL/min; DAD Wavelength range (nm): 210 to 500) Solvent Gradient: A=H$_2$O+5% MeOH+0.05% HCOOH, B=Acetonitrile+0.05% HCOOH) gradient: 0 min 10% B; 0-1.2 min 100% B; 1.2-1.50 min 100% B.

Method B:

Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 µm, 30×2.1 mm, Temp: 60° C., flow rate 0.85 mL/min; DAD Wavelength range (nm): 210 to 500) Solvent Gradient: A=H$_2$O+5% MeOH+0.05% HCOOH, B=Acetonitrile+0.05% HCOOH) gradient: 0 min 10% B; 0-2.7 min 100% B; 2.7-3.0 min 100% B.

Example 1: Preparation of Compound of Formula (VI-1-1/2)

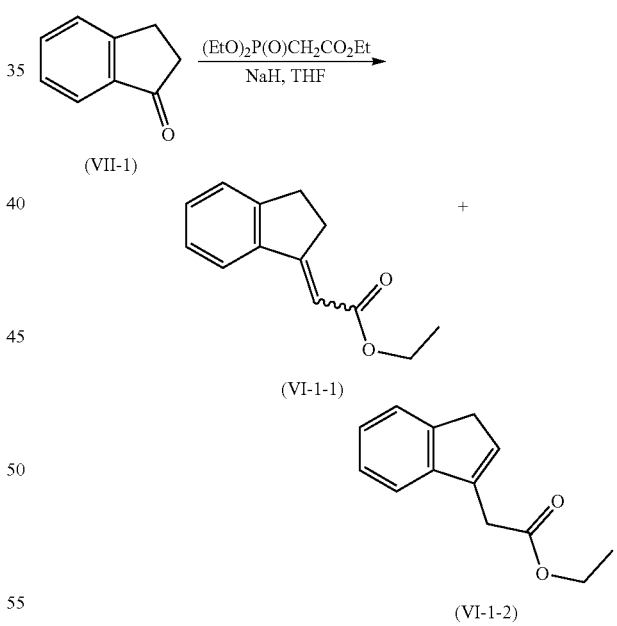

Under argon, ethyl 2-diethoxyphosphorylacetate (12 g, 54 mmol) was added to a suspension of sodium hydride (60 mass %, 2.3 g, 57 mmol) in 80 mL of dry tetrahydrofuran. The reaction mixture was then stirred for 15 min and a solution of compound of formula (VII-1) in 40 mL of tetrahydrofuran was added dropwise. The reaction mixture was then slowly warmed to room temperature and stirred at reflux. After 16 hours, the solution was poured into an aqueous HCl solution (300 ml, 1M) follow by extraction with ethyl acetate. The combined organic fractions were then washed with brine, dried over sodium sulfate and concentrated under reduce pressure. The crude reaction residue was purified by flash chromatography on silica gel affording compound of formula (VI-1) as a yellow oil and as a mixture of isomers in 59% yield (5.4 g, 27 mmol). LCMS: RT 1.09 min; ES+ 203 (M+H$^+$); $^1$H NMR (400 MHz, CDCl$_3$) meaningful signals for compound VI-1-1(E): δ ppm 6.47 (bs, 1H), 3.33 (m, 2H), 3.10 (m, 1H).

A Similar Procedure was Used to Prepare the Following Compounds:

(VI-76)

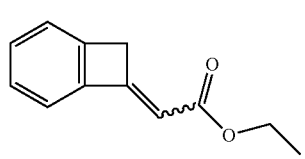

LCMS (Method A): RT 1.06 min, ES+ 189 (M+H$^+$); RT 1.17 min, ES+ 510 (M+H+); $^1$H NMR (400 MHz, CDCl$_3$) meaningful signals for compound VI-76 (E): δ ppm 7.19-7.39 (m, 4H), 6.02 (m, 1H), 4.22 (q, 2H), 4.01 (s, 2H), 1.31 (t, 3H).

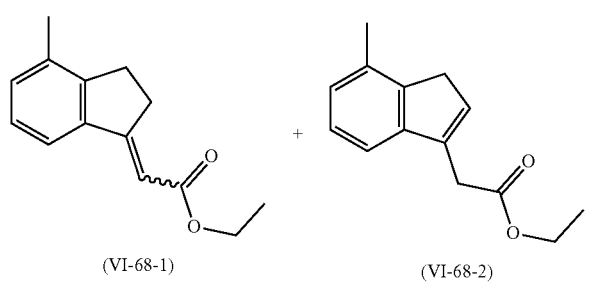 [SMILES: CCOC(=O)C=C1CCc2c(C)cccc21 ; CCOC(=O)CC1=CCc2c(C)cccc21]

(VI-68-1)          (VI-68-2)

LCMS (Method A): RT 1.11 and 1.18 min, ES+ 217 (M+H$^+$); $^1$H NMR (400 MHz, CDCl$_3$) meaningful signals for compound VI-68-1(E): δ ppm 7.00-7.47 (m, 3H), 6.29 (m, 1H), 4.23 (q, 2H), 3.31 (m, 2H), 2.97 (m, 2H), 2.29 (s, 3H), 1.33 (t, 3H).

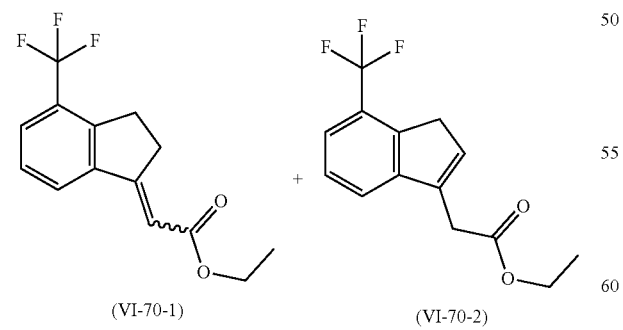

(VI-70-1)          (VI-70-2)

LCMS (Method A): RT 1.21 min, ES+ 271 (M+H$^+$); $^1$H NMR (400 MHz, CDCl$_3$) meaningful signals for compound VI-70-1(E): δ ppm 7.34-7.80 (m, 3H), 6.36 (m, 1H), 4.22 (q, 2H), 3.35 (m, 2H), 3.26 (m, 2H), 1.34 (t, 3H).

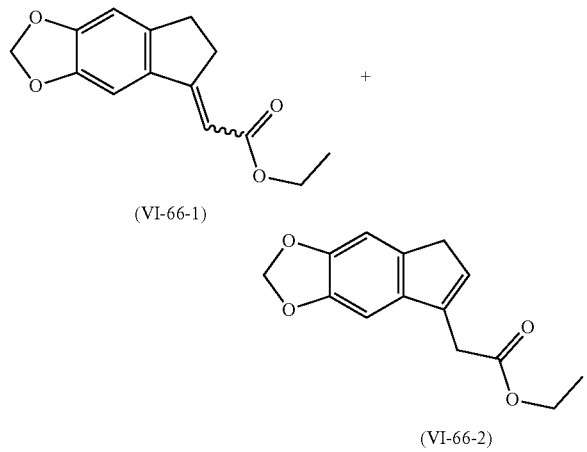

(VI-66-1)

(VI-66-2)

LCMS (Method A): RT 1.06 min, ES$^+$ 247 (M+H$^+$); $^1$H NMR (400 MHz, CDCl$_3$) meaningful signals for compound VI-66-1(E): δ ppm 6.97 (s, 1H), 6.76 (s, 1H), 6.07 (t, 1H), 6.00 (s, 2H), 4.21 (q, 2H), 3.27-3.33 (m, 2H), 2.97 (m, 2H), 1.32 (t, 3H).

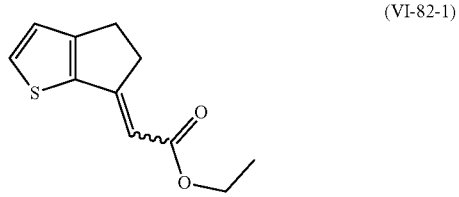

(VI-82-1)

LCMS (Method A): RT 1.07 min, ES$^+$ 209 (M+H$^+$); $^1$H NMR (400 MHz, CDCl$_3$) meaningful signals for compound VI-82-1(E): δ ppm 7.49 (d, 1H), 6.97 (d, 1H), 5.94 (m, 1H), 4.17 (q, 2H).

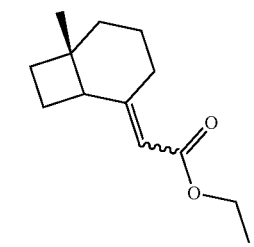

(VI-86)

LCMS (Method A): RT 1.25 min, ES$^+$ 209 (M+H$^+$)

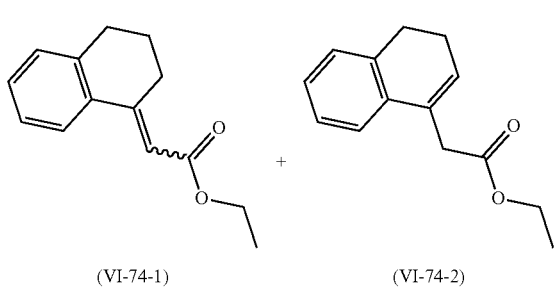 [SMILES: CCOC(=O)C=C1CCCc2ccccc21 ; CCOC(=O)CC1=CCCc2ccccc21]

(VI-74-1)          (VI-74-2)

LCMS (Method A): RT 1.11 and 1.17 min, ES⁺ 217 (M+H⁺)

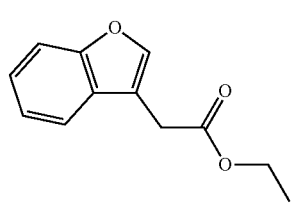

(VI-94-2)

$^1$H NMR (400 MHz, CDCl$_3$) δ ppm 7.63 (m, 1H), 7.58 (m, 1H), 7.48 (m, 1H), 7.31 (m, 1H), 7.25 (m, 1H), 4.20 (q, 2H), 3.70 (m, 2H), 1.27 (t, 3H).

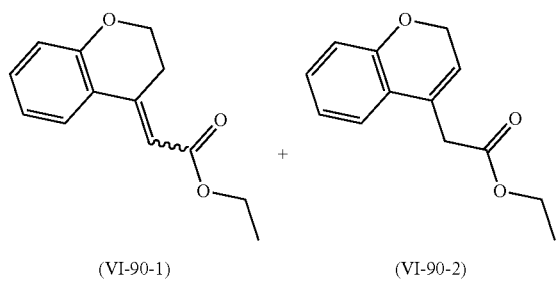 [SMILES: CCOC(=O)C=C1CCOc2ccccc21 ; CCOC(=O)CC1=CCOc2ccccc21]

(VI-90-1)          (VI-90-2)

LCMS (Method A): RT 1.00 and 1.07 min, ES⁺ 218 (M+H⁺)

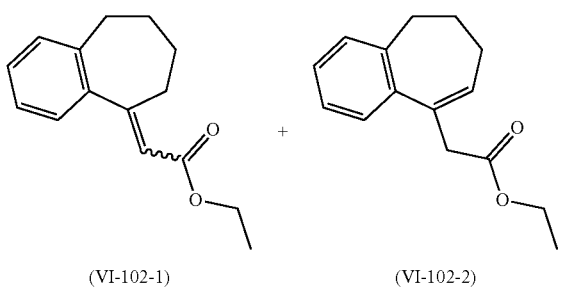 [SMILES: CCOC(=O)C=C1CCCCc2ccccc21 ; CCOC(=O)CC1=CCCCc2ccccc21]

(VI-102-1)         (VI-102-2)

LCMS (Method A): RT 1.15 and 1.22 min, ES⁺ 231 (M+H⁺)

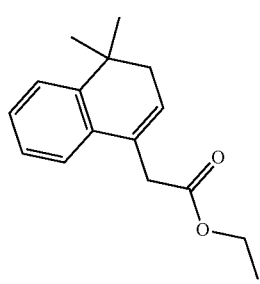

(VI-98-2)

$^1$H NMR (400 MHz, CDCl$_3$) δ ppm 7.31-7.36 (m, 1H), 7.16-7.26 (m, 3H), 5.93 (bt, 1H), 4.14 (q, 2H), 3.48 (bd, 2H), 2.27 (m, 2H), 1.57 (bs, 3H), 1.45 (bs, 3H), 1.21 (t, 3H).

Example 2: Preparation of Compound of Formula (VI-64)

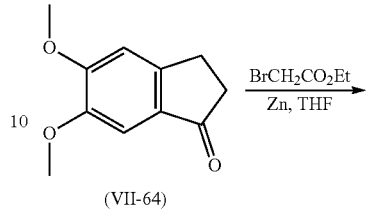

(VII-64)

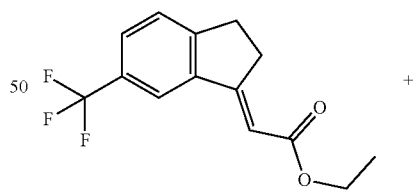

(VI-64)

In a sealed vial, known compound of formula (VII-64) (WO2008073452) (1.5 g, 7.8 mmol) was dissolved in tetrahydrofuran (15 mL) and ethyl 2-bromoacetate (2.6 g, 16 mmol) follow by Zinc (1.5 g, 23 mmol) was added. The resulting brown suspension was then heated to 70° C., stirred for 1 hour and quenched with a saturated aqueous NH$_4$Cl solution. 5 mL of an aqueous HCl (4N) solution was added and the reaction mixture was stirred for 5 minutes at room temperature. The phases were then separated follow by extraction with ethyl acetate and the combined organic fractions were dried over sodium sulfate and concentrated under vacuum. The resulting crude residue was purify by flash chromatography on silica gel and compound of formula (VI-64) was isolated in 64% yield (1.3 g, 5.0 mmol). LCMS: RT 1.01 min; ES+ 263 (M+H⁺); $^1$H NMR (400 MHz, CDCl$_3$): δ ppm 7.00 (s, 1H), 6.85 (s, 1H), 6.12 (m, 1H), 4.22 (q, 2H), 3.88 (s, 3H), 3.92 (s, 3H), 3.30 (m, 2H), 3.02 (m, 2H), 1.33 (t, 3H).

A Similar Procedure was Used to Prepare the Following Compounds:

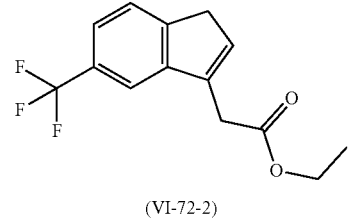

(VI-72-1)

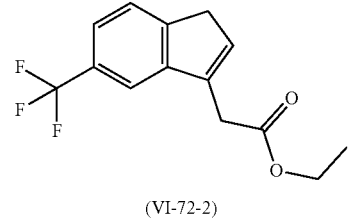

(VI-72-2)

Compound of formula (VI-72-1) and (VI-72-2) were obtained as a mixture of isomers as in example 1; LCMS (Method A): RT 1.14 and 1.19 min, ES– 279 (M–H⁺) and ES+ 271 (M+H⁺); ¹H NMR (400 MHz, CDCl₃) meaningful signals for compound VI-72-1(E): δ ppm 7.44-7.85 (m, 3H), 6.38 (m, 1H), 4.23 (q, 2H), 3.36 (m, 2H), 3.13 (m, 2H), 1.33 (t, 3H).

Example 3: Preparation of Compound of Formula (IVa-1)

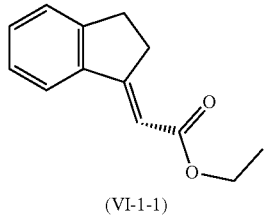
(VI-1-1)

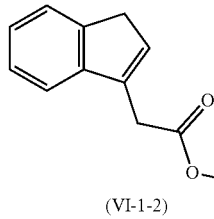
(VI-1-2)

H₂, Pd/C
Ethanol

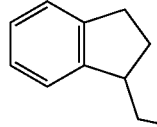
(IVa-1)

Under argon atmosphere, compounds of formula (VI-1-1/2) (3.16 g, 15.6 mmol) was dissolved in ethanol and Pd/C (1.56 mmol) was added. Argon was then replaced by hydrogen by two vacuum/H2 cycles and the resulting reaction mixture was stirred at room temperature under hydrogen atmosphere (1 bar). After 16 hours, the reaction was filtered on Celite® and the filter cake washed with ethanol. The solution was then concentrated under vacuum yielding to compound of formula (IV-1) as a yellow oil in 91% yield (2.9 g, 14 mmol). LCMS: RT 1.09 min; ES+ 205 (M+H⁺); ¹H NMR (400 MHz, CDCl₃): δ ppm 7.03-7.20 (m, 4H), 4.11 (q, 2H), 3.52 (m, 1H), 2.65-2.93 (m, 3H), 2.26-2.40 (m, 2H), 1.68 (m, 1H), 1.21 (t, 3H).

A Similar Procedure was Used to Prepare the Following Compounds:

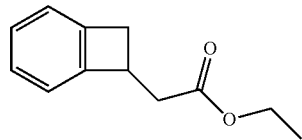
(VIa-76)

LCMS: RT 1.05 min; ES+ 191 (M+H⁺); ¹H NMR (400 MHz, CDCl₃): δ ppm 6.99-7.30 (m, 4H), 4.19 (q, 2H), 3.84 (m, 1H), 3.44 (dd, 1H), 2.85 (bd, 1H), 2.72 (m, 2H), 1.28 (t, 3H).

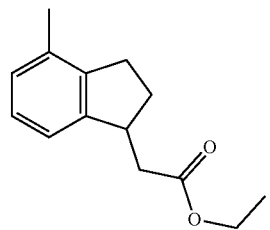
(IVa-68)

LCMS: RT 1.16 min; ES+ 219 (M+H⁺); ¹H NMR (400 MHz, CDCl₃): δ ppm 7.09 (m, 1H), 7.00 (m, 2H), 4.18 (q, 2H), 3.59 (m, 1H), 2.82-2.92 (m, 1H), 2.71-2.82 (m, 2H), 2.34-2.46 (m, 2H), 2.26 (s, 3H), 1.75 (m, 1H), 1.28 (t, 3H).

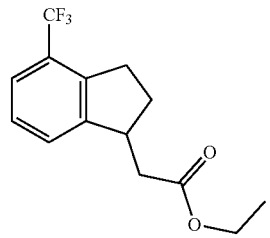
(IVa-70)

LCMS: RT 1.19 min; ES+ 273 (M+H⁺); ¹H NMR (400 MHz, CDCl₃): δ ppm 7.44 (m, 1H), 7.35 (m, 1H), 7.26 (m, 1H), 4.19 (q, 2H), 3.61 (m, 1H), 3.08-3.20 (m, 1H), 2.95-3.07 (m, 1H), 2.75 (dd, 1H), 2.38-2.52 (m, 2H), 1.82 (m, 1H), 1.28 (t, 3H).

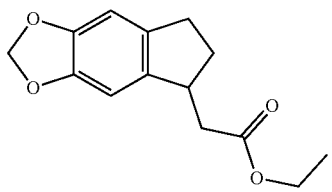
(IVa-66)

LCMS: RT 1.05 min; ES+ 249 (M+H⁺); ¹H NMR (400 MHz, CDCl₃): δ ppm 6.68 (bs, 1H), 6.65 (bs, 1H), 5.91 (m, 2H), 4.18 (q, 2H), 3.49 (m, 1H), 2.71-2.88 (m, 2H), 2.67 (dd, 1H), 2.33-2.43 (m, 2H), 1.76 (m, 1H), 1.28 (t, 3H).

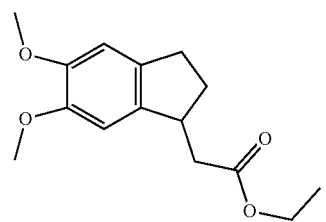
(IVa-64)

LCMS: RT 1.00 min; ES+ 265 (M+H⁺); ¹H NMR (400 MHz, CDCl₃): δ ppm 6.76 (s, 1H), 6.73 (s, 1H), 4.18 (q, 2H), 3.86 (s, 3H), 3.85 (s, 3H), 2.76-2.94 (m, 2H), 2.71 (dd, 1H), 2.33-2.46 (m, 2H), 1.77 (m, 1H), 1.28 (t, 3H).

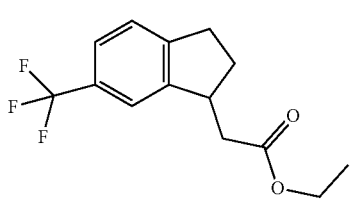 (IVa-72)

LCMS: RT 1.18 min; ES+ 273 (M+H+); $^1$H NMR (400 MHz, CDCl$_3$): δ ppm 7.39-7.46 (m, 2H), 7.29-7.34 (m, 1H), 4.19 (m, 1H), 3.63 (m, 1H), 2.85-3.04 (m, 2H), 2.77 (dd, 1H), 2.38-2.54 (m, 2H), 1.82 (m, 1H), 1.27 (t, 3H).

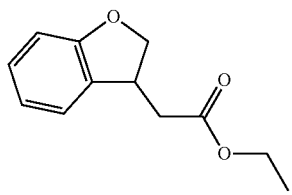 (IVa-94)

LCMS: RT 0.97 min; ES+ 207 (M+H+); $^1$H NMR (400 MHz, CDCl$_3$): δ ppm 7.10-7.20 (m, 2H), 6.86 (m, 1H), 6.80 (m, 1H), 4.75 (t, 1H), 4.26 (dd, 1H), 4.18 (q, 2H), 3.83-3.92 (m, 1H), 2.79 (dd, 1H), 2.58 (dd, 1H), 1.28 (t, 3H).

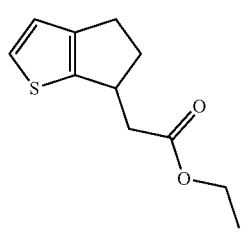 (IVa-82)

LCMS: RT 1.07 min; ES+ 211 (M+H+); $^1$H NMR (400 MHz, CDCl$_3$): δ ppm 7.20 (d, 1H), 6.81 (d, 1H), 4.22 (q, 2H), 3.69 (m, 1H), 2.85-2.69 (m, 3H), 2.67-2.54 (m, 2H), 2.19-2.10 (m, 1H).

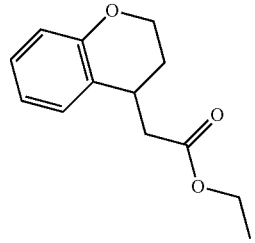 (IVa-90)

LCMS: RT 1.01 min; ES+ 221 (M+H+); $^1$H NMR (400 MHz, CDCl$_3$): δ ppm 7.07-7.14 (m, 2H), 6.86 (m, 1H), 6.80 (m, 1H), 4.13-4.24 (m, 4H), 3.36 (m, 1H), 2.79 (dd, 1H), 2.52 (dd, 1H), 2.16 (m, 1H), 1.79-1.90 (m, 1H), 1.28 (t, 3H).

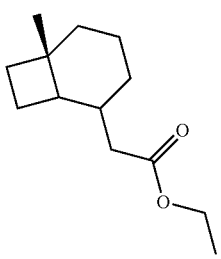 (IVa-86)

$^1$H NMR (400 MHz, CDCl$_3$): (data given for both diastereoisomers) δ ppm 4.12 (q, 4H), 1.38-2.28 (m, 27H), 1.25 (t, 6H), 1.22-1.28 (m, 2H), 1.12 (s, 3H), 1.01 (s, 3H).

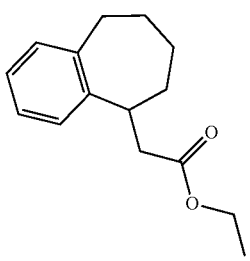 (IVa-102)

LCMS: RT 1.19 min; ES+ 233 (M+H+); $^1$H NMR (400 MHz, CDCl$_3$): δ ppm) 7.05-7.17 (m, 4H), 4.13 (q, 2H), 3.48 (m, 1H), 2.76-2.97 (m, 3H), 2.69 (dd, 1H), 1.66-1.94 (m, 4H), 1.47-1.64 (m, 2H), 1.22 (t, 3H).

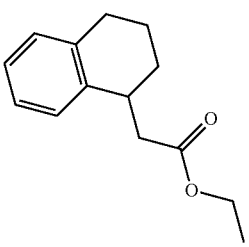 (IVa-74)

LCMS: RT 1.14 min; ES+ 219 (M+H+); $^1$H NMR (400 MHz, CDCl$_3$): δ ppm 7.03-7.19 (m, 4H), 4.17 (q, 2H), 3.35 (m, 1H), 2.73-2.83 (m, 2H), 2.70 (dd, 1H), 2.52 (dd, 1H), 1.65-1.97 (m, 4H), 1.27 (t, 3H).

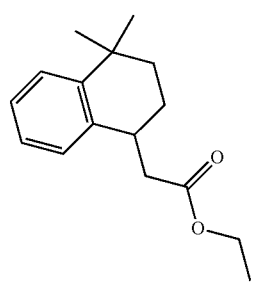 (IVa-98)

LCMS: RT 1.21 min; ES+ 247 (M+H+); $^1$H NMR (400 MHz, CDCl$_3$): δ ppm) 7.35 (m, 1H), 7.10-7.22 (m, 3H), 4.20

(q, 2H), 3.36 (dq, 1H), 2.69 (dd, 1H), 2.57 (dd, 1H), 2.00 (m, 1H), 1.79 (m, 1H), 1.67-1.75 (m, 1H), 1.51-1.64 (m, 1H), 1.24-1.36 (m, 9H).

Example 4: Preparation of Compound of Formula (IVb-28)

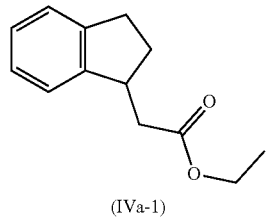

Compound of formula (IVa-1) (9.3 g, 46 mmol) was dissolved in tetrahydrofuran (90 mL) and methanol (46 mL) and a solution of lithium hydroxide (2.2 g, 91 mmol) in water (46 mL) was added dropwise. The resulting solution was stirred at room temperature for 1 hour and the volatiles were removed under reduce pressure. The aqueous residue was then acidified using an aqueous HCl solution (2M) and diluted with ethyl acetate. The phases were separated and the organic phase was washed with brine, dried over sodium sulfate and concentrated under vacuum. Compound of formula (IVb-28) was obtained as a white solid in quantitative yield (46 mmol). LCMS: RT 0.85 min; ES+ 177 (M+H$^+$); $^1$H NMR (400 MHz, CDCl$_3$): δ ppm 7.13-7.29 (m, 4H), 3.60 (m, 1H), 2.80-3.02 (m, 3H), 2.37-2.56 (m, 2H), 1.73-1.85 (m, 1H).

Example 4: Preparation of Compound of Formula (IVa-10)

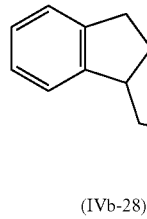

Compound of formula (IVb-28) (0.80 g, 4.5 mmol) was dissolved in methanol (14 mL), sulfuric acid was added dropwise (0.026 mL, 0.45 mmol) and the resulting reaction mixture was stirred for 16 hours at 70° C. Water was then added and the pH adjusted to 7/8 using a saturated aqueous NaHCO$_3$ solution. The aqueous phase was extracted with ethyl acetate and the combined organic extracts were dried over sodium sulfate and concentrated under vacuum. The crude reaction residue was purified by flash chromatography on silica gel and compound of formula (IVa-10) was obtained as a light yellow oil in 98% yield (0.85 g, 4.47 mmol). $^1$H NMR (400 MHz, CDCl$_3$): δ ppm 7.12-7.34 (m, 4H), 3.75 (s, 3H), 3.62 (m, 1H), 2.85-3.02 (m, 2H), 2.81 (dd, 1H), 2.36-2.52 (m, 2H), 1.77 (m, 1H).

A Similar Procedure was Used to Prepare the Following Compound:

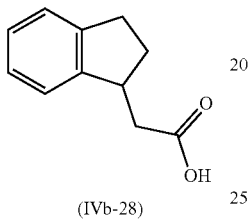

$^1$H NMR (400 MHz, CDCl$_3$): δ ppm 7.16-7.28 (m, 4H), 3.59 (m, 1H), 2.84-3.02 (m, 2H), 2.73 (1H, dd), 2.34-2.46 (m, 2H), 1.79 (m, 1H), 1.51 (s, 9H).

Example 5: Preparation of Compound of Formula (IVc-37)

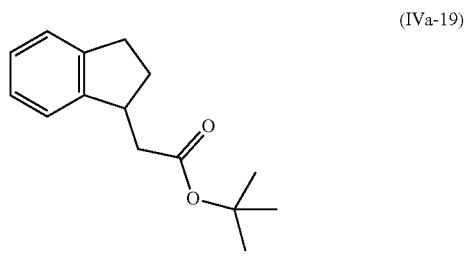 [SMILES: CC(C)(C)OC(=O)CC1CCc2ccccc21]

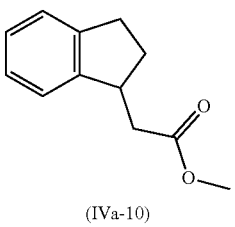

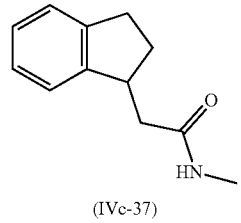

Under argon atmosphere, compound of formula (IVb-28) (2.0, 11 mmol) and one drop of dimethylformamide (DMF) was solved in dichloromethane (33 mL) and oxalyl chloride (1.26 mL, 13.2 mmol) was then added dropwise. The resulting reaction mixture was stirred for 3 hours at room temperature, purged with nitrogen and the volatiles were removed under vacuum. The resulting crude residue was then dissolved in tetrahydrofuran (THF, 22 mL), the solution cooled to 0° C., and methylamine (2M in THF, 16 mL, 33.0 mmol) was carefully added (dropwise) over 10 minutes. The reaction mixture was slowly warmed to room temperature and stirred for 3 hours. The suspension was then diluted with dichloromethane and washed with an aqueous HCl solution (0.5M). The phases were separated and the organic phase was dried over sodium sulfate and concentrated under vacuum. The crude reaction residue was purified by flash chromatography on silica gel yielding to compound of formula (IVc-37) as a beige solid in 96% yield (2.0 g, 11 mmol). LCMS: RT 0.75 min; ES+ 190 (M+H$^+$); $^1$H NMR (400 MHz, CDCl$_3$): δ ppm 7.14-7.27 (m, 4H), 5.42 (bs, 1H), 3.67 (m, 1H), 2.80-3.01 (m, 5H), 2.63 (dd, 1H), 2.40 (m, 1H), 2.31 (dd, 1H), 1.76 (m, 1H).

Example 6: Preparation of Compound of Formula (IVd-37)

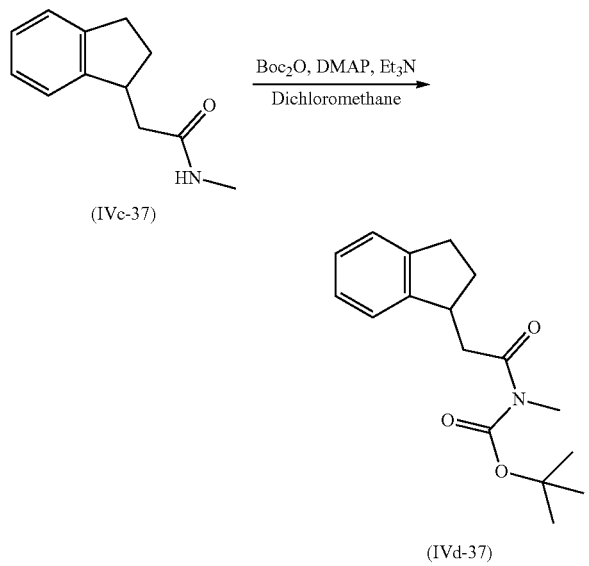

Compound of formula (IVc-37) (0.58 g, 2.85 mmol) was dissolved in dichloromethane, Boc$_2$O (1.3 g, 5.87 mmol), Et$_3$N (0.50 mL, 3.52 mmol) and DMAP (0.04 g, 0.29 mmol) was added and the resulting solution was stirred for 16 hours at room temperature. The reaction mixture was then diluted with dichloromethane and washed with an aqueous HCl (0.5M) solution, a saturated aqueous NaHCO$_3$ solution and brine. The phases were separated and the organic phase was dried over sodium sulfate and concentrated under vacuum. The crude yellow oil was then purify by flash chromatography on silica gel affording compound of formula (IVd-37) as a yellow oil in 97% yield (0.87 g, 2.86 mmol). $^1$H NMR (400 MHz, CDCl$_3$): δ ppm 7.11-7.28 (m, 4H), 3.67 (m, 1H), 3.38 (dd, 1H), 3.18 (s, 3H), 2.80-3.03 (m, 3H), 2.41 (m, 1H), 1.70 (m, 1H), 1.51 (bs, 9H).

Example 7: Preparation of Compound of Formula (IIIa-1)

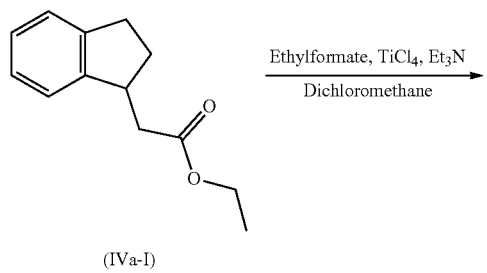

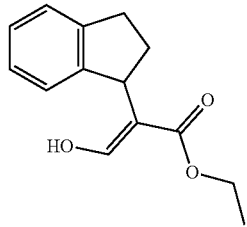

Compound of formula (Iva-1) (1.0 g, 4.89 mmol) was dissolved in dichloromethane (14.7 mL) and ethyl formate was added. The resulting reaction mixture was cooled to 0° C. and TiCl4 (1.07 mL, 9.79 mmol) was added dropwise followed by slow addition of Et$_3$N (1.63 mL, 11.7 mmol). The resulting solution was then stirred for 1.5 hours at 0° C., diluted with dichloromethane and quenched with ice-water. The organic phase was washed three times with water, dried over sodium sulfate and concentrated under vacuum. The crude reaction residue was purified by flash chromatography on silica gel affording compound of formula (IIa-I) as a yellow oil (mixture of isomer, Z/E-enol and aldehyde) in 96% yield (1.15 g, 4.70 mmol). LCMS: RT 1.17 min; ES-231 (M-H$^+$).

A Similar Procedure was Used to Prepare the Following Compounds:

| Compounds | | LCMS (method A) |
|---|---|---|
| (IIa-76) | | 1.16 min; 217 (M – H$^+$) |
| (IIa-70) | | 1.26 min; 299 (M – H$^+$) |
| (IIa-68) | | 1.25 min; 245 (M – H$^+$) |
| (IIa-66) | | 1.14 min; 275 (M – H$^+$) |

| Compounds | LCMS (method A) |
|---|---|
| (IIa-64) | 1.09 min; 291 (M − H⁺) |
| (IIa-72) | 1.23 min; 301 (M + H⁺) |
| (IIa-10) | 1.10 min; 217 (M − H⁺) |
| (IIa-82) | 1.16 min; 237 (M − H⁺) |
| (IIa-86) | 1.32 min; 237 (M − H⁺) |
| (IIa-74) | 0.91 min; 233 (M + H⁺) |
| (IIa-94) | 1.03 min; 233 (M − H⁺) |
| (IIa-90) | 1.09 min; 248 (M − H⁺) |
| (IIa-102) | 1.24 min; 259 (M − H⁺) |
| (IIa-98) | 1.30 min; 273 (M − H⁺) |

Example 8: Preparation of Compound of Formula (IIa-19)

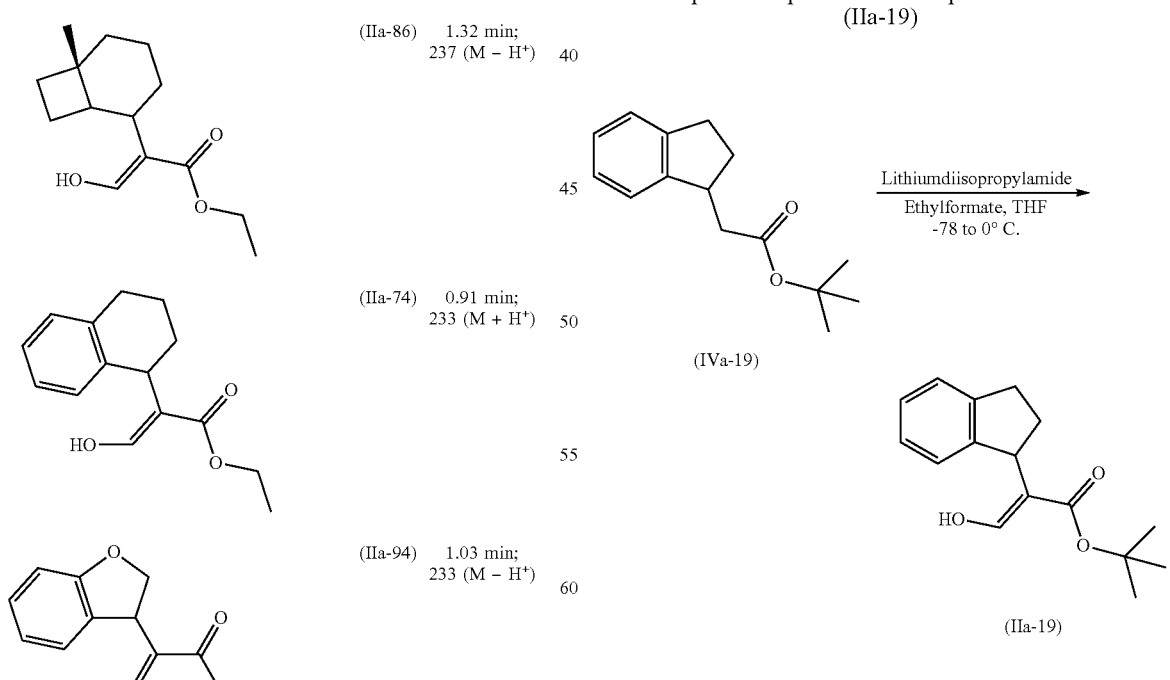

Compound of formula (Iva-19) (0.2 g, 0.86 mmol) was dissolved in tetrahydrofurane (2.6 mL), the solution cooled to −78° C. and a solution of lithiumdiisopropylamide (0.16 mL, 1.3 mmol) was slowly added dropwise. After 30 min at −78° C., ethyl formate (0.19 g, 2.58 mmol) was added dropwise and the resulting reaction mixture was allowed to warm to room temperature and further stirred for 3 hours. The reaction was then diluted with ethyl acetate and quenched with an aqueous HCl solution (0.50 M) until pH reached 6. The phases were separated, the aqueous phase extracted with ethyl acetate and the combined organic fractions were dried over sodium sulfate, concentrated under vacuum affording compound of formula (IIa-19) as an orange oil in 93% yield (0.22 g, 0.80 mmol). LCMS: RT 1.30 min; ES− 259 (M−H$^+$).

Example 9: Preparation of Compound of Formula (IId-37)

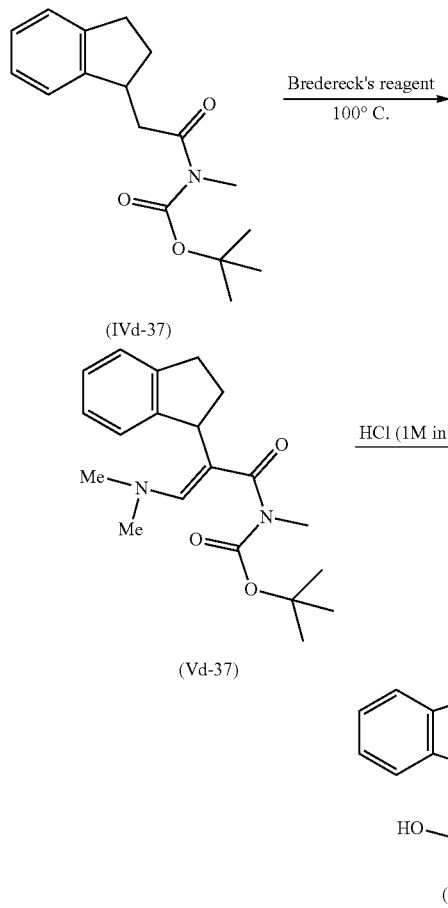

Compound of formula (IVd-37) (0.37 g, 1.28 mmol) was treated with Bredereck's reagent (1.24 g, 1.47 mL, 4.39 mmol) and the reaction mixture was heated to 100° C. and stirred for 9 hours. The reaction mixture was then diluted with ethyl acetate (90 ML) and washed with water (35 mL) and brine (35 mL). The phases were separated and the organic phase was dried over sodium sulfate and concentrated under vacuum affording compound of formula (Vd-37) as a a crude brown oil in 87% yield (0.48 g, 1.11 mmol) which was progressed in the next step without further purification.

Compound of formula (Vd-37) (0.48 g, 1.11 mmol) was dissolved in dioxane (4.5 mL), aqueous HCl (1M, 1.11 mL) was added and the resulting solution was stirred for 4 hours at room temperature. Saturated aqueous NaHCO$_3$ solution was added followed by ethyl acetate (30 mL). After vigorous stirring for 5 minutes, the phases were separated and the organic fraction was washed with brine, dried over sodium sulfate and concentrated under vacuum affording compound of formula (IId-37) (0.3 g, 0.97 mmol) which was progressed in the next step without further purification.

Example 10: Preparation of Compound of Formula (I-1)

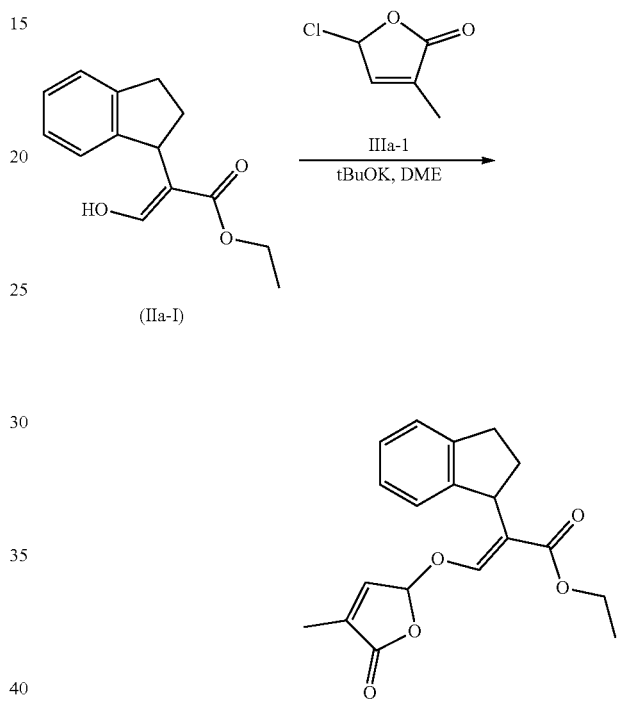

Compound of formula (IIa-1) (0.15 g, 0.61 mmol) was dissolved in anhydrous 1,2-dimethoxyethane (4 mL), the resulting solution cooled to 0° C. and tBuOK (0.08 g, 0.73 mmol) was then added. After 10 minutes at 0° C., known compound of formula (IIIa-1) (0.1 g, 0.74 mmol) was added as a solution in 1 mL of DME. The reaction mixture was then slowly warmed to room temperature. After 16 hours, a saturated aqueous NH4Cl solution was added and the reaction mixture was extracted with ethyl acetate. The combined organic extracts were washed with brine, dried over sodium sulfate and concentrated under vacuum. The crude reaction residue was purified by flash chromatography on silica gel affording compound of formula (I-1) as a colorless oil and as a mixture of diastereoisomers in 60% yield (0.12 g, 0.36 mmol). LCMS: RT 1.09 min; ES+ (M+H$^+$); $^1$H NMR (400 MHz, CDCl$_3$) Data given for one diastereoisomers: δ ppm 7.56 (bs, 1H), 6.86-7.13 (m, 4H), 6.74 (m, 1H), 6.01 (bs, 1H), 4.38 (m, 1H), 4.03 (q, 2H), 2.91-3.01 (m, 1H), 2.77-2.88 (m, 1H), 2.24 (m, 1H), 2.08 (m, 1H), 1.89 (m, 3H), 1.09 (t, 3H).

A Similar Procedure was Used to Prepare the Following Compounds:

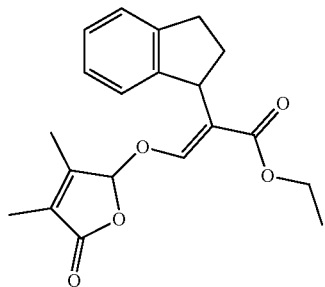
(I-2)

Using compound known compound 2-chloro-3,4-dimethyl-2H-furan-5-one (IIIa-2) (WO 2012/056113).

LCMS: RT 1.13 min; ES+ 343 (M+H$^+$); $^1$H NMR (400 MHz, CDCl$_3$) Data given for the two diastereoisomers: δ ppm 7.58 (bs, 1H), 7.53 (bs, 1H), 6.87-7.13 (m, 8H), 5.79 (bs, 1H), 5.65 (bs, 1H), 4.38 (bt, 2H), 4.09 (q, 2H), 4.02 (m, 2H), 2.75-3.01 (m, 4H), 2.19-2.30 (m, 2H), 1.99-2.12 (m, 2H), 1.76 (bs, 3H), 1.74 (bs, 3H), 1.50 (bs, 3H), 1.48 (bs, 3H), 1.15 (t, 3H), 1.07 (t, 3H).

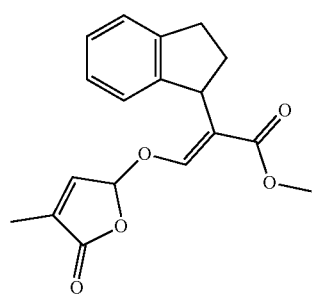
(I-10)

Using compound (IIIa-1). LCMS: RT 1.03 min; ES+ 315 (M+H$^+$); $^1$H NMR (400 MHz, CDCl$_3$) Data given for the two diastereoisomers: δ ppm 7.65 (bs, 1H), 7.63 (bs, 1H), 6.96-7.24 (m, 8H), 6.81 (m, 1H), 6.65 (m, 1H), 6.08 (m, 1H), 6.00 (m, 1H), 4.47 (td, 2H), 3.69 (s, 3H), 3.66 (s, 3H), 3.01-3.11 (m, 2H), 2.86-2.97 (m, 2H), 2.28-2.38 (m, 2H), 2.13-2.23 (m, 2H), 1.98 (m, 6H),

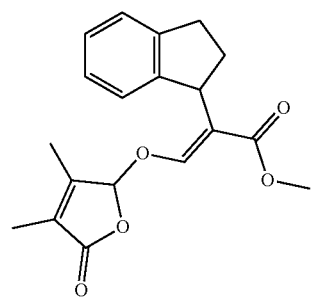
(I-11)

Using compound (IIIa-2). LCMS: RT 1.07 min; ES+ 329 (M+H$^+$); $^1$H NMR (400 MHz, CDCl$_3$) Data given for the two diastereoisomers: δ ppm 7.67 (bs, 1H), 7.62 (bs, 1H), 6.97-7.23 (m, 8H), 5.87 (s, 1H), 5.74 (s, 1H), 4.48 (m, 2H), 3.73 (s, 3H), 3.67 (s, 3H), 2.86-3.12 (m, 4H), 2.30-2.40 (m, 2H), 2.09-2.24 (m, 2H), 1.88 (bs, 3H), 1.85 (bs, 3H), 1.83 (bs 3H), 1.56 (m, 3H).

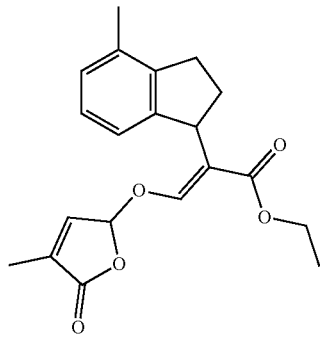
(I-68)

Using compound (IIIa-1). LCMS: RT 1.15 min; ES+ 343 (M+H$^+$); $^1$H NMR (400 MHz, CDCl$_3$) Data given for the two diastereoisomers: δ ppm 7.61 (bs, 1H), 7.60 (bs, 1H), 6.97-7.04 (m, 2H), 6.89-6.96 (m, 2H), 6.77-6.85 (m, 3H), 6.66 (m, 1H), 6.09 (bs, 1H), 6.00 (bs, 1H), 4.46 (m, 2H), 4.02-4.14 (m, 4H), 2.92-3.04 (m, 2H), 2.73-2.84 (m, 2H), 2.24 (bs, 6H), 2.07-2.38 (m, 4H), 1.97 (m, 6H), 1.15 (q, 3H), 1.14 (q, 3H).

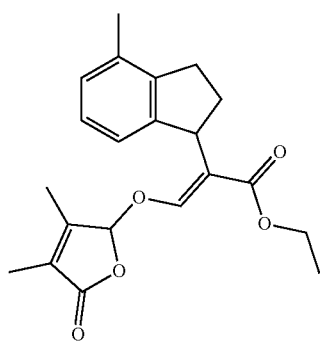
(I-69)

Using compound (IIIa-2). LCMS: RT 1.19 min; ES+ 357 (M+H$^+$); $^1$H NMR (400 MHz, CDCl$_3$) Data given for the two diastereoisomers: δ ppm 7.63 (bs, 1H), 7.60 (bs, 1H), 6.96-7.05 (m, 2H), 6.88-6.95 (m, 2H), 6.77-6.87 (m, 2H), 5.87 (bs, 1H), 5.73 (bs, 1H), 4.46 (m, 2H), 4.03-4.19 (m, 4H), 2.87-3.05 (m, 2H), 2.71-2.85 (m, 2H), 2.24 (s, 3H), 2.23 (s, 3H), 1.94-2.40 (m, 4H), 1.84 (s, 3H), 1.82 (s, 3H), 1.57 (s, 3H), 1.54 (s, 3H), 1.22 (t, 3H), 1.14 (t, 3H).

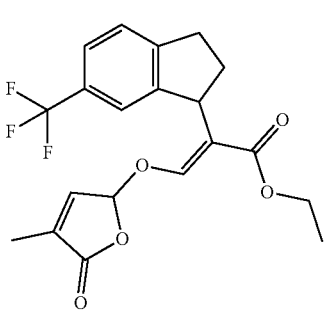
(I-72)

Using compound (IIIa-1). LCMS: RT 1.16 min; ES+ 397 (M+H⁺); ¹H NMR (400 MHz, CDCl₃) Data given for the two diastereoisomers: δ ppm 7.66 (bs, 1H), 7.65 (bs, 1H), 7.38 (bs, 1H), 7.37 (bs, 1H), 7.28 (bs, 1H), 7.26 (bs, 1H), 7.23 (bs, 1H), 7.19 (bs, 1H), 6.84 (m, 1H), 6.61 (m, 1H), 6.11 (m, 1H), 6.00 (m, 1H), 4.46 (t, 2H), 4.01-418 (m, 4H), 3.00.3.15 (m, 2H), 2.87-2.99 (m, 2H), 2.32-2.44 (m, 2H), 2.09-2.27 (m, 4H), 1.98 (m, 3H), 1.95 (m, 3H), 1.18 (m, 3H), 1.12 (m, 3H).

(I-73)

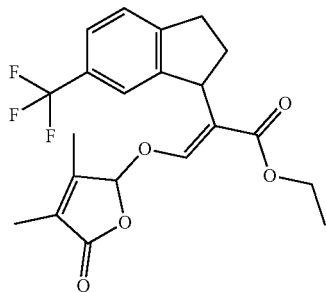

Using compound (IIIa-2). LCMS: RT 1.19 min; 419 ES– (M−H⁺); ¹H NMR (400 MHz, CDCl₃) Data given for the two diastereoisomers: δ ppm 7.68 (s, 1H), 7.64 (s, 1H), 7.38 (bs, 1H), 7.36 (bs, 1H), 7.24-7.31 (m, 3H), 7.19 (bs, 1H), 5.89 (bs, 1H), 5.72 (bs, 1H), 4.47 (t, 2H), 4.19 (q, 2H), 4.03-4.15 (m, 2H), 2.86-3.15 (m, 4H), 2.34-2.45 (m, 2H), 2.05-2.29 (m, 2H), 1.87 (bs, 3H), 1.85 (bs, 3H), 1.80 (bs, 3H), 1.46 (bs, 3H), 1.25 (t, 3H), 1.14 (t, 3H).

(I-64)

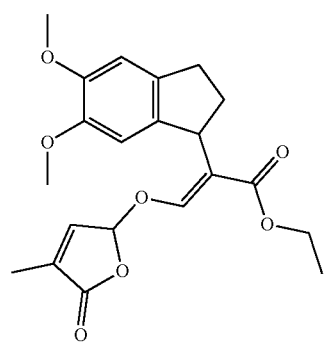

Using compound (IIIa-1). ¹H NMR (400 MHz, CDCl₃) Data given for the two diastereoisomers: δ ppm 7.60 (bs, 1H), 7.58 (bs, 1H), 6.83 (m, 1H), 6.75 (m, 1H), 6.72 (bs, 2H), 6.53 (bs, 1H), 6.49 (bs, 1H), 6.10 (m, 1H), 6.03 (m, 1H), 4.41 (td, 2H), 4.05-4.14 (m, 4H), 3.85 (s, 2H), 3.84 (s, 3H), 3.81 (s, 3H), 3.79 (s, 3H), 2.94-3.03 (m, 2H), 2.79-2.90 (m, 2H), 2.32 (m, 2H), 2.11-2.21 (m, 2H), 1.98 (m, 6H), 1.17 (t, 3H), 1.15 (t, 3H).

(I-65)

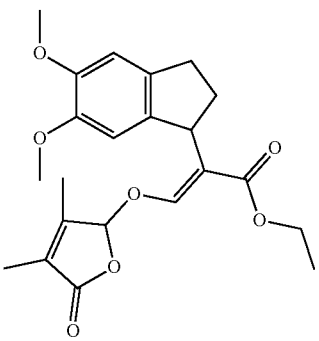

Using compound (IIIa-2). LCMS: RT 1.04 min; 402 ES+(M+H⁺); ¹H NMR (400 MHz, CDCl₃) Data given for the two diastereoisomers: δ ppm 7.63 (bs, 1H), 7.57 (bs, 1H), 6.72 (bs, 2H), 6.55 (bs, 1H), 6.50 (bs, 1H), 5.87 (bs, 1H), 5.76 (bs, 1H), 4.42 (t, 2H), 4.06-4-19 (m, 4H), 3.84 (s, 6H), 3.81 (s, 3H), 3.78 (s, 3H), 2.78-3.02 (m, 4H), 2.28-2.40 (m, 2H), 2.08-2.20 (m, 2H), 1.88 (bs, 3H), 1.84 (bs, 3H), 1.83 (bs, 3H), 1.68 (bs, 3H), 1.22 (t, 3H), 1.17 (t, 2H).

(I-66)

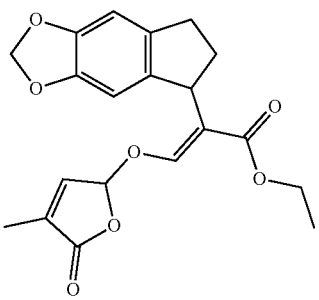

Using compound (IIIa-1). LCMS: RT 1.06 min; 373 ES+ (M+H⁺); ¹H NMR (400 MHz, CDCl₃) Data given for the two diastereoisomers: δ ppm 7.61 (bs, 1H), 7.59 (bs, 1H), 6.86 (m, 1H), 6.77 (m, 1H), 6.64 (bs, 1H), 6.63 (bs, 1H), 6.46 (bs, 1H), 6.43 (bs, 1H), 6.09 (m, 1H), 6.03 (m, 1H), 5.86-5.90 (m, 4H), 4.35 (t, 2H), 4.05-4.16 (m, 4H), 2.88.2-97 (m, 2H), 2.13-2.23 (m, 2H), 1.99 (m, 6H), 1.19 (t, 3H), 1.18 (t, 3H).

(I-70)

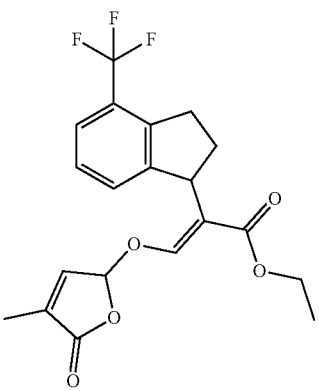

Using compound (IIIa-1). LCMS: RT 1.19 min; ES+ 397 (M+H⁺); ¹H NMR (400 MHz, CDCl₃) Data given for the two diastereoisomers: δ ppm 7.64 (bs, 1H), 7.60 (bs, 1H), 7.33-7.42 (m, 1H), 7.13-7.22 (m, 2H), 6.77 (bs, 1H), 6.86 (bs, 1H), 6.04 (bs, 1H), 6.00 (bs, 1H), 4.48 (m, 2H), 4.10 (q, 4H), 3.17-3.30 (m, 2H), 2.96-3.09 (m, 2H), 2.39 (m, 2H), 2.15 (m, 2H), 1.97 (s, 3H), 1.93 (s, 3H), 1.15 (t, 6H).

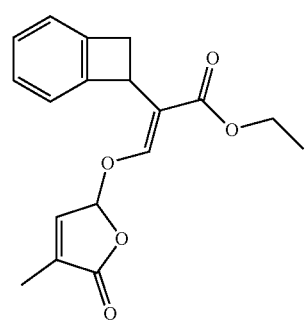

(I-76)

Using compound (IIIa-1). LCMS: RT 1.07 min; ES+ 315 (M+H+); $^1$H NMR (400 MHz, CDCl$_3$) Data given for the two diastereoisomers: δ ppm 7.55 (bs, 1H), 7.54 (bs, 1H), 7.09-7.20 (m, 2H), 6.97-7.04 (m, 2H), 6.80 (m, 1H), 6.70 (m, 1H), 6.03 (m, 1H), 6.00 (m, 1H), 4.58 (m, 1H), 4.07-4.17 (m, 4H), 3.44-3.53 (m, 2H), 3.26 (td, 2H), 1.96-2.00 (m, 6H), 1.17 (t, 3H), 1.16 (t, 3H).

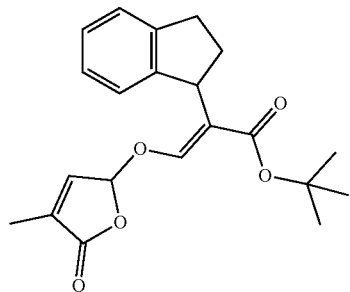

(I-19)

Using compound (IIIa-1). $^1$H NMR (400 MHz, CDCl$_3$) Data given for the two diastereoisomers: δ ppm 7.55 (s, 2H), 7.16-7.22 (m, 2H), 7.08-7.14 (m, 4H), 6.96-7.04 (m, 2H), 6.85 (m, 1H), 6.72 (m, 1H), 6.11 (m, 1H), 6.03 (m, 1H), 4.44 (m, 2H), 2.87-3.07 (m, 4H), 2.26-2.36 (m, 2H), 2.12-2.24 (m, 2H), 1.99 (m, 6H), 1.31 (s, 9H), 1.27 (s, 9H).

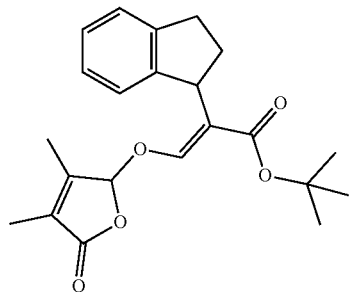

(I-20)

Using compound (IIIa-2). $^1$H NMR (400 MHz, CDCl$_3$) Data given for the two diastereoisomers: δ ppm 7.56 (bs, 1H), 7.55 (bs, 1H), 6.97-7.21 (m, 81H), 5.89 (bs, 1H), 5.77 (bs, 1H), 4.45 (bt, 2H), 2.95 (m, 2H), 2.28-2.38 (m, 2H), 2.03-2.24 (m, 4H), 1.93 (bs, 3H), 1.86 (bs, 3H), 1.84 (bs, 3H), 1.64 (bs, 3H), 1.38 (s, 9H), 1.29 (s, 9H).

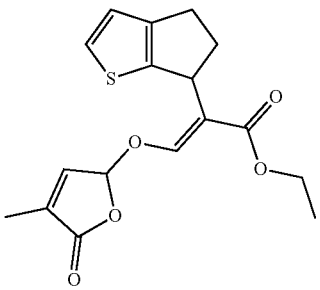

(I-82)

Using compound (IIIa-1). LCMS: RT 1.06 min; ES+ 335 (M+H+); $^1$H NMR (400 MHz, CDCl$_3$) Data given for the two diastereoisomers: δ ppm 7.53 (bs, 1H), 7.51 (bs, 1H), 7.13 (m, 2H), 6.87 (m, 1H), 6.73 (m, 2H), 6.69 (m, 1H), 6.08 (m, 1H), 5.98 (m, 1H), 4.53-4.46 (m, 2H), 4.19-4.07 (m, 4H), 2.93-2.80 (m, 2H), 2.79-2.66 (m, 4H), 2.53-2.42 (m, 2H), 1.99 (m, 3H), 1.98 (m, 3H), 1.22 (t, 3H), 1.18 (t, 3H).

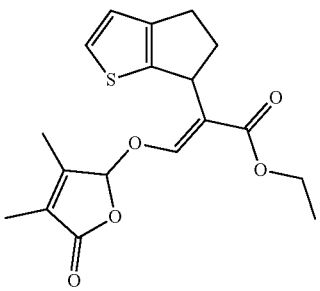

(I-83)

Using compound (IIIa-2). LCMS: RT 1.11 min; ES+ 349 (M+H+); $^1$H NMR (400 MHz, CDCl$_3$) Data given for the two diastereoisomers: δ ppm 7.57 (s, 1H), 7.51 (s, 1H), 7.12 (m, 1H), 6.72 (m, 1H), 5.87 (bs, 1H), 5.75 (bs, 1H), 4.48-4.55 (m, 2H), 4.08-4.22 (m, 4H), 2.66-2.83 (m, 6H), 2.39-2.55 (m, 2H), 1.93 (m, 3H), 1.86 (m, 3H), 1.84 (m, 3H), 1.68 (m, 3H), 1.26 (t, 3H), 1.20 (t, 3H).

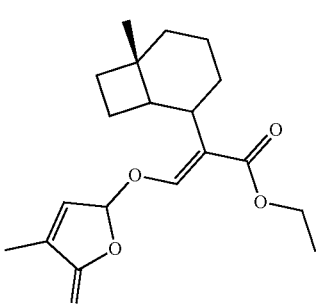

(I-86)

Using compound (IIIa-1). (I-86) obtained and isolated as a mixture of diastereoisomers. LCMS: RT 1.21 min; ES+ 335 (M+H+).

(I-74)

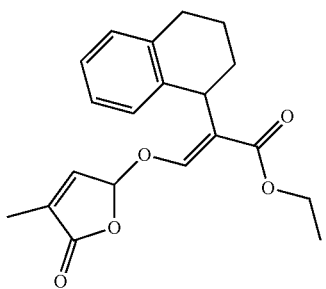

Using compound (IIIa-1). ¹H NMR (400 MHz, CDCl₃) LCMS: RT 1.12 min; ES+ 343 (M+H⁺); ¹H NMR (400 MHz, CDCl₃) Data given for the two diastereoisomers: δ ppm 7.62 (s, 1H), 7.61 (s, 1H), 6.91-7.06 (m, 8H), 6.80 (m, 1H), 6.62 (m, 1H), 6.08 (m, 1H), 5.96 (m, 1H), 4.11-4.18 (m, 2H), 4.00-4.10 (m, 4H), 2.69-2.88 (m, 4H), 1.89-1.99 (m, 12H), 1.14 (t, 3H), 1.10 (t, 3H).

(I-75)

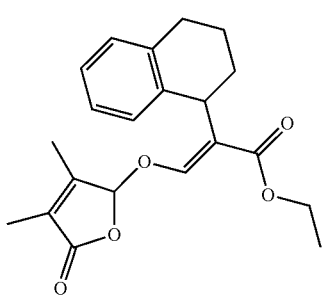

Using compound (IIIa-2). ¹H NMR (400 MHz, CDCl₃) LCMS: RT 1.16 min; ES+ 357 (M+H⁺); ¹H NMR (400 MHz, CDCl₃) Data given for the two diastereoisomers: δ ppm 7.62 (s, 1H), 7.60 (s, 1H), 6.92-7.05 (m, 8H), 5.86 (bs, 1H), 5.71 (bs, 1H), 4.00-4.20 (m, 6H), 2.70-2.87 (m, 4H), 1.87-2.00 (m, 9H), 1.80-1.85 (m, 6H), 1.64-1.76 (m, 2H), 1.54 (m, 3H), 1.20 (t, 3H), 1.12 (t, 3H).

(I-7)

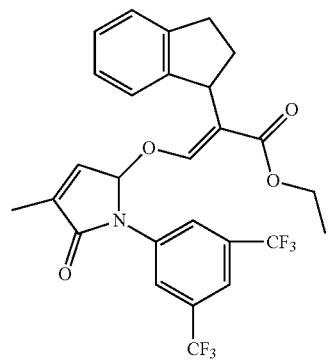

Using compound (IIIb, WO2015/128321). LCMS: RT 1.31 min; ES− 538 (M−H⁺); ¹H NMR (400 MHz, CDCl₃) Data given for the two diastereoisomers: δ ppm 8.16 (bs, 4H), 7.69 (bs, 1H), 7.66 (bs, 1H), 7.36 (s, 1H), 7.31 (s, 1H), 7.12-7.17 (m, 2H), 7.06 (m, 2H), 6.97-7.03 (m, 1H), 6.94 (m, 1H), 6.80 (m, 1H), 6.74 (m, 1H), 6.66 (m, 1H), 6.59 (m, 1H), 6.18 (m, 1H), 6.11 (m, 1H), 4.41 (m, 2H), 3.95-4.09 (m, 4H), 2.79-3.04 (m, 4H), 2.19-2.29 (m, 1H), 1.95-2.12 (m, 9H), 1.09 (t, 3H), 1.03 (t, 3H).

(I-94)

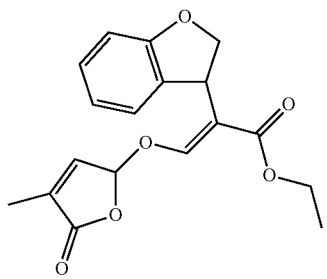

Using compound (IIIa-1). ¹H NMR (400 MHz, CDCl₃) LCMS: RT 0.98 min; ES+ 331 (M+H⁺); ¹H NMR (400 MHz, CDCl₃) Data given for the two diastereoisomers: δ ppm 7.66 (bs, 1H), 7.63 (bs, 1H), 7.06-7.14 (m, 2H), 6.98-7.05 (m, 2H), 6.73-6.85 (m, 5H), 6.68 (m, 1H), 6.10 (m, 1H), 6.00 (m, 1H), 4.77-4.85 (m, 2H), 4.67-4.75 (m, 2H), 4.45-4.52 (m, 2H), 4.08-4.22 (m, 4H), 2.00 (m, 3H), 1.98 (m, 3H), 1.20 (t, 3H), 1.17 (t, 3H).

(I-95)

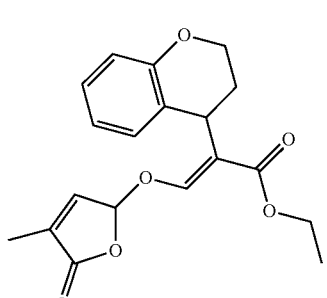

Using compound (IIIa-2). ¹H NMR (400 MHz, CDCl₃) LCMS: RT 1.02 min; ES+ 345 (M+H⁺); ¹H NMR (400 MHz, CDCl₃) Data given for the two diastereoisomers: δ ppm 7.70 (bs, 1H), 7.63 (bs, 1H), 6.98-7.14 (m, 4H), 6.71-6.86 (m, 4H), 5.87 (bs, 1H), 5.76 (bs, 1H), 4.78-4.88 (m, 2H), 4.67-4.77 (m, 2H), 4.41-4.52 (m, 2H), 4.10-4.20 (m, 4H), 1.91 (m, 3H), 1.86 (m, 3H), 1.85 (m, 3H), 1.64 (m, 3H), 1.28 (t, 3H), 1.20 (t, 3H).

(I-90)

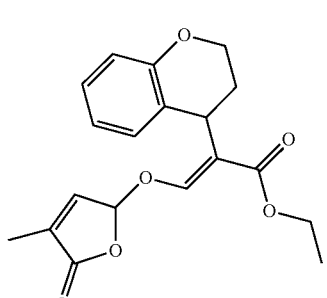

Using compound (IIIa-1). ¹H NMR (400 MHz, CDCl₃) LCMS: RT 1.01 min; ES+ 345 (M+H⁺); ¹H NMR (400 MHz, CDCl₃) Data given for the two diastereoisomers: δ ppm 7.66 (bs, 1H), 7.63 (bs, 1H), 6.99-7.09 (m, 2H), 6.88-6.96 (m, 2H), 6.71-6.81 (m, 5H), 6.50 (m, 1H), 6.04 (m, 1H), 5.90 (m, 1H), 4.04-4.34 (m, 10H), 2.22-2.36 (m, 2H), 1.92-2.02 (m, 8H), 1.18 (t, 3H), 1.15 (t, 3H).

MHz, CDCl$_3$) Data given for the two diastereoisomers: δ ppm 7.76 (bs, 1H), 7.73 (bs, 1H), 7.03-7.13 (m, 6H), 6.96-7.01 (m, 2H), 5.90 (bs, 1H), 5.88 (bs, 1H), 4.25-4.30 (m, 2H), 4.18 (q, 4H), 2.89-3.01 (m, 2H), 2.74-2.86 (m, 2H), 1.81-2.03 (m, 22H), 1.30-1.40 (m, 2H), 1.27 (t, 6H).

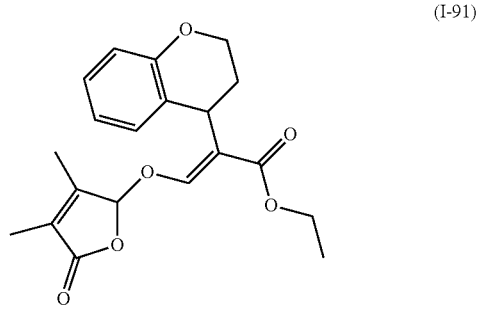 [SMILES: CCOC(=O)/C(=C/OC1OC(=O)C(C)=C1C)C1CCOc2ccccc21]

(I-91)

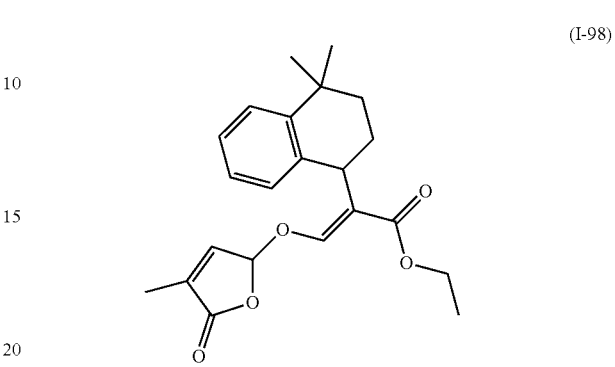

(I-98)

Using compound (IIIa-2). $^1$H NMR (400 MHz, CDCl$_3$) LCMS: RT 1.04 min; ES+ 359 (M+H$^+$); $^1$H NMR (400 MHz, CDCl$_3$) Data given for the two diastereoisomers: δ ppm 7.66 (bs, 1H), 7.62 (bs, 1H), 6.95-7.06 (m, 3H), 6.91 (m, 1H), 6.70-6.81 (m, 3H), 5.82 (bs, 1H), 5.66 (bs, 1H), 4.05-4.32 (m, 10H), 2.17-2.32 (m, 2H), 1.93-2.05 (m, 2H), 1.87 (m, 3H), 1.80 (m, 6H), 1.47 (m, 3H), 1.25 (t, 3H), 1.17 (t, 3H).

Using compound (IIIa-1). $^1$H NMR (400 MHz, CDCl$_3$) LCMS: RT 1.20 min; ES+ 371 (M+H$^+$)

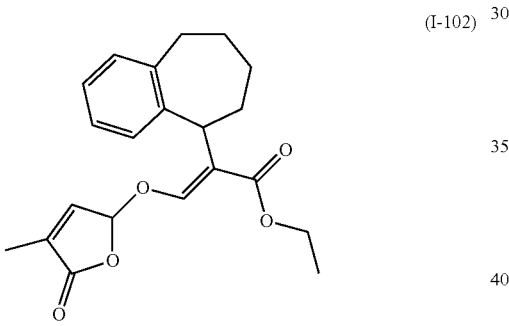

(I-102)

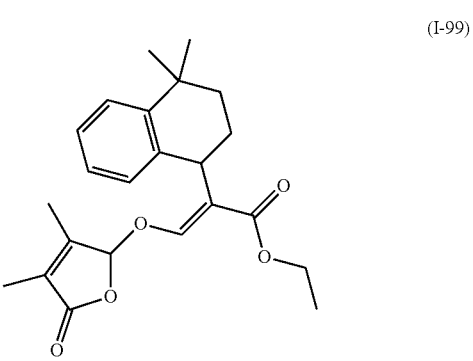

(I-99)

Using compound (IIIa-1). $^1$H NMR (400 MHz, CDCl$_3$) LCMS: RT 1.13 min; ES+ 357 (M+H$^+$); $^1$H NMR (400 MHz, CDCl$_3$) Data given for the two diastereoisomers: δ ppm 7.74 (bs, 1H), 7.72 (bs, 1H), 7.04-7.14 (m, 6H), 6.94-7.00 (m, 2H), 6.84 (m, 2H), 6.11 (m, 1H), 6.08 (m, 1H), 4.23-4.29 (m, 2H), 4.18 (m, 4H), 2.73-3.00 (m, 5H), 1.83-2.04 (m, 15H), 1.29-1.42 (m, 2H), 1.27 (t, 3H), 1.26 (t, 3H).

Using compound (IIIa-2). $^1$H NMR (400 MHz, CDCl$_3$) LCMS: RT 1.23 min; ES+ 385 (M+H$^+$)

Example 10: Preparation of Compound of Formula (I-37)

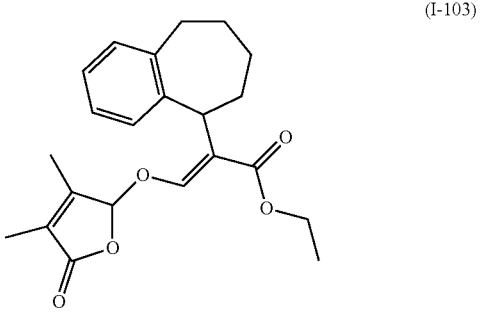 [SMILES: CCOC(=O)/C(=C/OC1OC(=O)C(C)=C1C)C1CCCCc2ccccc21]

(I-103)

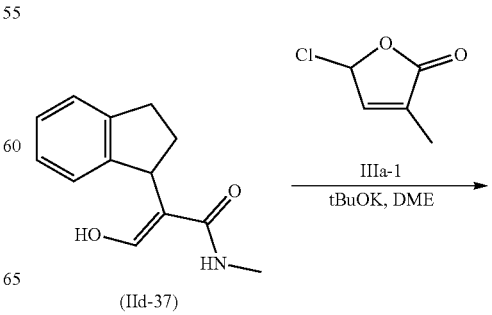

Using compound (IIIa-2). $^1$H NMR (400 MHz, CDCl$_3$) LCMS: RT 1.17 min; ES+ 371 (M+H$^+$); $^1$H NMR (400

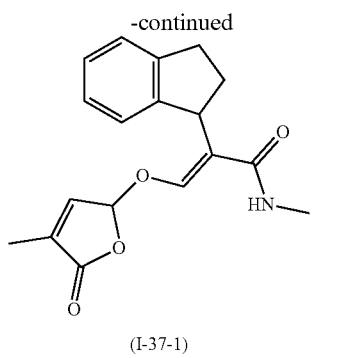

(I-37-1)

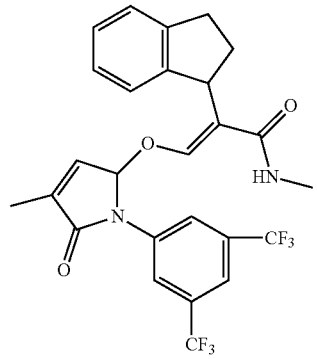

(I-55-1)

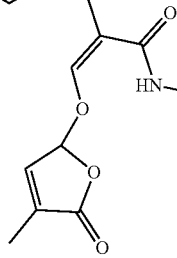

(I-37-2)

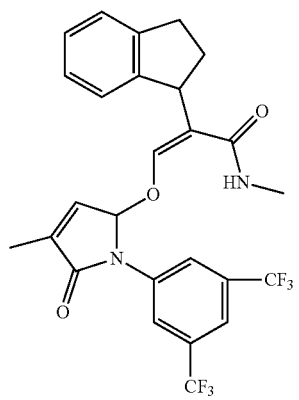

(I-55-2)

Compound of formula (IId-37) (0.27 g, 0.74 mmol) was dissolved in anhydrous 1,2-dimethoxyethane (6 mL), the resulting solution cooled to 0° C. and tBuOK (0.10 g, 0.89 mmol) was then added. After 10 minutes at 0° C., known compound of formula (IIIa-1) (0.11 g, 0.89 mmol) was added as a solution in 1.4 mL of DME. The reaction mixture was then slowly warmed to room temperature. After 3 hours, a saturated aqueous NH4Cl solution was added and the reaction mixture was extracted with ethyl acetate. The combined organic extracts were washed with brine, dried over sodium sulfate and concentrated under vacuum. The crude reaction residue was purified and the isomers separated by flash chromatography on silica gel affording compound of formula (I-37-1) (0.033 g, 0.10 mmol) and compound of formula (I-37-2) (0.087 g, 0.28 mmol) in 14 and 37% yield respectively.

Compound of formula (I-37-1) LCMS: RT 0.88 min; ES+ 314 (M+H$^+$); $^1$H NMR (400 MHz, CDCl$_3$) Data given for the two diastereoisomers: δ ppm 7.52 (s, 2H), 7.07-7.23 (m, 8H), 6.87 (m, 1H), 6.84 (m, 1H), 6.14 (m, 1H), 6.11 (m, 1H), 4.99 (m, 2H), 4.56 (m, 2H), 2.86-3.06 (m, 4H), 2.61-2.65 (m, 6H), 2.27-2.40 (m, 2H), 1.94-2.06 (m, 8H).

Compound of formula (I-37-2) LCMS: RT 0.87 min; ES+ 314 (M+H$^+$); $^1$H NMR (400 MHz, CDCl$_3$) Data given for the two diastereoisomers: δ ppm 7.09-7.26 (m, 8H), 6.87 (m, 2H), 6.64 (bs, 1H), 6.55 (bs, 1H), 6.20 (s, 1H), 6.19 (s, 1H), 5.93 (m, 1H), 5.90 (m, 1H), 4.37 (m, 2H), 2.79-3.00 (m, 10H), 2.48 (m, 2H), 1.98 (bs, 6H), 1.84-1.94 (m, 2H).

An identical procedure was used to prepare compounds of formula (I-55-1/2) using intermediate (IIIb, WO2015/128321):

LCMS (I-55-1): RT 1.12 min; ES− 523 (M−H$^+$); LCMS (I-55-2): RT 1.16 min; ES− 523 (M−H$^+$);

A Similar Synthetic Route was Used to Prepare the Following Compounds:

For compound numbers with a suffix, the suffix refers to different isomeric forms, for example I-49-1 and I-49-2 refer to the E and Z isomers respectively of compound I-49.

Compound of Formula (I-49-1)

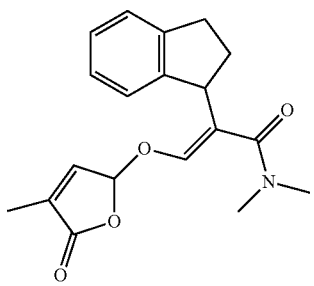

LCMS: RT 0.91 min; ES+ 328 (M+H$^+$); $^1$H NMR (400 MHz, CDCl$_3$) Data given for the two diastereoisomers: δ ppm 7.08-7.23 (m, 8H), 6.79 (m, 2H), 6.48 (bs, 2H), 6.01 (m, 2H), 4.34 (t, 2H), 2.80-3.03 (m, 4H), 2.94 (bs, 12H), 2.30-2.40 (m, 2H), 2.06-2.16 (m, 2H), 1.95 (m, 6H).

Compound of Formula (I-49-2)

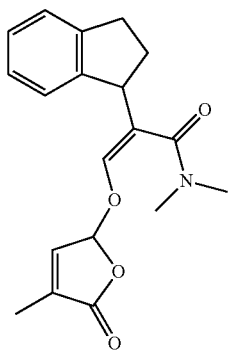 [SMILES: CC1=CC(O/C=C(\C(=O)N(C)C)C2CCc3ccccc32)OC1=O]

LCMS: RT 0.88 min; ES+ 328 (M+H+); $^1$H NMR (400 MHz, CDCl$_3$) Data given for the two diastereoisomers: δ ppm 7.13-7.32 (8H), 6.84 (m, 2H), 6.00 (m, 1H), 5.95 (m, 1H), 5.90 (m, 1H), 5.88 (m, 1H), 4.08 (m, 1H), 3.98 (m, 1H), 2.76-3.04 (m, 4H), 2.97 (bs, 3H), 2.95 (bs, 3H), 2.91 (bs, 3H), 2.89 (bs, 3H), 2.26-2.38 (m, 2H), 2.01-2.16 (m, 2H), 1.95 (m, 6H).

Example B1—Corn Seed Germination

The effect of compounds of formula (I) on the germination of NK Falkone 2015 corn seeds under cold stress was evaluated as follows. NK Falkone corn seeds were sorted by size using 2 sieves, one excluding very big seeds and the other with round holes of 8 to 9 mm diameter. The seeds retained by the latter sieve were used for the germination test. The corn seeds were placed in 24 well plates (each plate was considered as one experimental unit or replicate). Germination was initiated by the addition of 250 µl of distilled water containing 0.5% DMSO per well as a means for compound solubilization. 8 replicates (ie, 8 plates) were used for each treatment characterization. Plates were sealed using seal foil (Polyolefin Art. Nr. 900320) from HJ-BIO-ANALYTIK. All plates were placed horizontally on trolleys in a climatic chamber at 15° C. The experiment was laid out in a completely randomized design in climatic chamber with 75% Relative Humidity. Foils were pierced, one hole per well using a syringe after 72 hours for experiments performed at 15° C.

Germination was followed over time by taking photographs at different time points. Image analysis was performed automatically with a macro which was developed using the Image J software. A dynamic analysis of germination was carried out by fitting a logistic curve. Three parameters were calculated from the logistic curve: the T50; the slope and the plateau. All three parameters have a high agronomical relevance and are key requirements to ensure a good early crop-establishment. The T50 and slope for compounds tested are shown in Table 2 below. All the values are expressed as percentages compared to an untreated control. All the three parameters are calculated considering 8 replicates and the kinetic parameters are separately determined for each germination curve. Data in bold indicate germination enhancing statistically significant differences between treated seeds and untreated control (p<0.05). The T50 corresponds to the time needed for half of the seed population to germinate. Higher negative %-values indicate faster germination. The slope indicates how synchronous the germination of the seed population is. Positive values indicate steeper curve; the steeper the curve, the better and more uniform the germination is.

TABLE 2

Effect of strigolactone analogues on germination of Falkone 2015 corn seeds under cold stress condition (15° C.) at various concentrations.

| Compound | Reference | Rate (µM)[a] | Slope (% vs control)[b] | T50 (% vs control)[b] |
|---|---|---|---|---|
| Prior art 1: GR24 | J. Chem. Soc., Perkin Trans. 1: Organic and Bio-Organic Chemistry, 1981, 6, 1734-1743 | 2<br>10<br>50<br>250 | −0.7<br>−11.3<br>6.2<br>36.3 | −1.5<br>−0.1<br>−1.85<br>−3.40 |
| Prior art 2 | Plant Physiology, 2012, 159, 1524-1544 | 2<br>10<br>50<br>250 | −1.3<br>1.4<br>9.6<br>15.8 | −1.5<br>1.7<br>−1.6<br>−2.1 |

TABLE 2-continued

Effect of strigolactone analogues on germination of Falkone 2015 corn seeds under cold stress condition (15° C.) at various concentrations.

| Compound | Reference | Rate (μM)[a] | Slope (% vs control)[b] | T50 (% vs control)[b] |
|---|---|---|---|---|
| Prior art 3 | J. Chem. Soc., Perkin Trans. 1: Organic and Bio-Organic Chemistry, 1981, 6, 1734-1743 | 2<br>10<br>50<br>250 | −0.7<br>2.2<br>4.0<br>14.1 | 1.6<br>0<br>−0.8<br>−0.5 |
| Prior art 4 | J. Agrlc. Food Chem. 40, 1992, 1222-1229 | 2<br>10<br>50<br>250 | −7.7<br>14.9<br>−11.4<br>4.1 | 1.2<br>−3.4<br>2.4<br>0.1 |
| Prior art 5 (R=Et) | J. Agrlc. Food Chem. 40, 1992, 1222-1229 (R=Me) | 2<br>10<br>50<br>250 | 0.9<br>7.4<br>21.8<br>23.9 | 3.1<br>1.8<br>−0.7<br>−2.7 |
| Compound I-1 | n/a | 2<br>10<br>50<br>250 | 8.1<br>10.0<br>27.9<br>142.0 | −0.5<br>1.6<br>−2.8<br>−7.2 |

TABLE 2-continued

Effect of strigolactone analogues on germination of Falkone 2015 corn seeds under cold stress condition (15° C.) at various concentrations.

| Compound | Reference | Rate (μM)[a] | Slope (% vs control)[b] | T50 (% vs control)[b] |
|---|---|---|---|---|
| 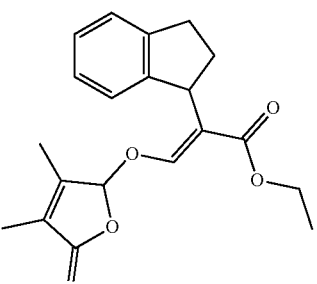<br>Compound I-2 | n/a | 2<br>10<br>50<br>250 | −11.8<br>18.1<br>47.0<br>121.2 | 2.3<br>−3.0<br>−6.2<br>−10.1 |
| 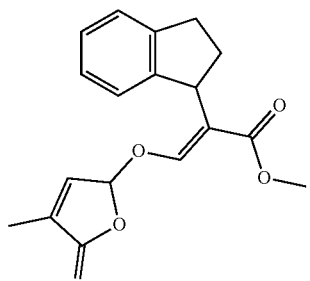<br>Compound I-10 | n/a | 2<br>10<br>50<br>250 | 8.2<br>10.7<br>30.3<br>82.5 | −0.9<br>−0.8<br>−3.3<br>−7.4 |
| 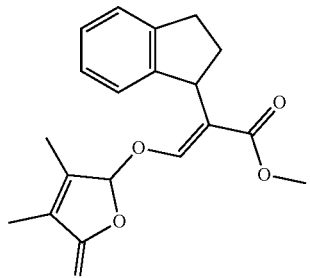<br>Compound I-11 | n/a | 2<br>10<br>50<br>250 | 11.4<br>7.4<br>20.1<br>89.6 | −1.0<br>0.2<br>−5.1<br>−6.9 |
| 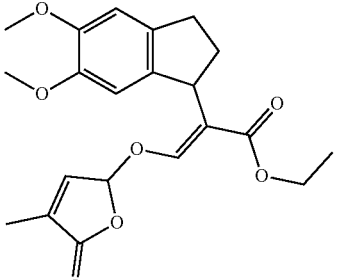<br>Compound I-64 | n/a | 2<br>10<br>50<br>250 | 1.1<br>−1.6<br>27.9<br>83.8 | −1.4<br>−3.2<br>−4.6<br>−10.7 |

TABLE 2-continued

Effect of strigolactone analogues on germination of Falkone 2015 corn seeds under cold stress condition (15° C.) at various concentrations.

| Compound | Reference | Rate (μM)[a] | Slope (% vs control)[b] | T50 (% vs control)[b] |
|---|---|---|---|---|
| Compound I-65 | n/a | 2<br>10<br>50<br>250 | 1.0<br>18.8<br>23.0<br>122.9 | −0.9<br>−3.1<br>−2.6<br>−12.6 |
| Compound I-76 | n/a | 0.4<br>2<br>10<br>50 | −5.6<br>−5.0<br>50.6<br>121.6 | −0.5<br>−0.7<br>−6.4<br>−8.8 |
| Compound I-73 | n/a | 2<br>10<br>50<br>250 | −1.1<br>14.2<br>57.8<br>54.1 | −3.5<br>−6.3<br>−7.8<br>−9.2 |
| Compound I-70 | n/a | 2<br>10<br>50<br>250 | 9.0<br>18.4<br>87.9<br>114.6 | −2.5<br>−0.2<br>−6.8<br>−8.6 |

TABLE 2-continued

Effect of strigolactone analogues on germination of Falkone 2015 corn seeds under cold stress condition (15° C.) at various concentrations.

| Compound | Reference | Rate (μM)[a] | Slope (% vs control)[b] | T50 (% vs control)[b] |
|---|---|---|---|---|
| Compound I-68 | n/a | 2 | 23.4 | −1.2 |
|  |  | 10 | 3.8 | −0.6 |
|  |  | 50 | 44.7 | −5.7 |
|  |  | 250 | 112.7 | −6.8 |
| Compound I-66 | n/a | 2 | 22.6 | −5.2 |
|  |  | 10 | 2.9 | −2.9 |
|  |  | 50 | 34.5 | −5.1 |
|  |  | 250 | 31.6 | −5.8 |
| Compound I-83 | n/a | 2 | 6.5 | −3.0 |
|  |  | 10 | 34.1 | −2.2 |
|  |  | 50 | 32.6 | −4.8 |
|  |  | 250 | 157.2 | −8.6 |
| Compound I-75 | n/a | 2 | 4.9 | −3.5 |
|  |  | 10 | 5.6 | −2.6 |
|  |  | 50 | 58.4 | −6.5 |
|  |  | 250 | 44.2 | −5.0 |

TABLE 2-continued

Effect of strigolactone analogues on germination of Falkone 2015 corn seeds under cold stress condition (15° C.) at various concentrations.

| Compound | Reference | Rate (μM)[a] | Slope (% vs control)[b] | T50 (% vs control)[b] |
|---|---|---|---|---|
| Compound I-55-1 | n/a | 2 | −8.1 | 1.7 |
| | | 10 | 3.8 | −1.4 |
| | | 50 | 61.1 | −6.8 |
| | | 250 | 89.8 | −10.6 |
| Compound I-7 | n/a | 2 | 63.9 | −3.4 |
| | | 10 | 69.8 | −3.5 |
| | | 50 | 78.8 | −6.6 |
| | | 250 | 11.3 | −1.8 |
| Compound I-37-1 | n/a | 2 | 10.8 | −1.3 |
| | | 10 | −15.7 | −2.5 |
| | | 50 | 5.2 | −2.6 |
| | | 250 | 51.7 | −4.6 |
| Compound I-86 | n/a | 2 | 17.1 | 0.2 |
| | | 10 | 20.2 | −2.7 |
| | | 50 | 138.3 | −9.7 |
| | | 250 | 149.9 | −11.2 |

TABLE 2-continued

Effect of strigolactone analogues on germination of Falkone 2015 corn seeds under cold stress condition (15° C.) at various concentrations.

| Compound | Reference | Rate (µM)[a] | Slope (% vs control)[b] | T50 (% vs control)[b] |
|---|---|---|---|---|
| 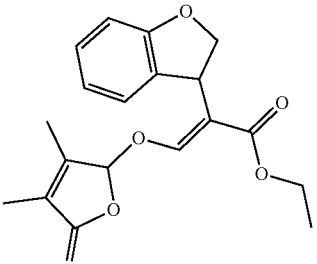<br>Compound I-95 | n/a | 2<br>10<br>50<br>250 | −2.0<br>−13.9<br>2.7<br>81.5 | 1.6<br>1.6<br>0.6<br>−6.7 |
| 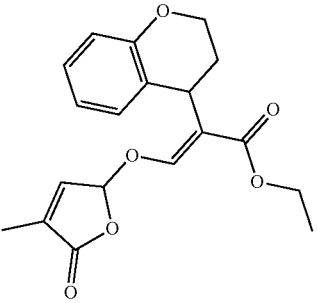 [SMILES: CCOC(=O)/C(=C/OC1C=C(C)C(=O)O1)C1CCOc2ccccc21]<br>Compound I-90 | n/a | 2<br>10<br>50<br>250 | −10<br>−0.32<br>4.6<br>83.6 | 3.2<br>2.8<br>0.45<br>−6.7 |
| 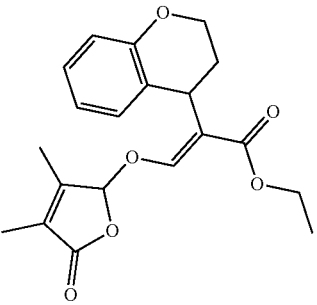 [SMILES: CCOC(=O)/C(=C/OC1OC(=O)C(C)=C1C)C1CCOc2ccccc21]<br>Compound I-91 | n/a | 2<br>10<br>50<br>250 | −15.3<br>−5.4<br>18.8<br>67.4 | 2.5<br>2.7<br>−1.5<br>−6.1 |

[a]Concentration of compound in 250µl distilled water containing 0.5% DMSO
[b]Control = 250µl distilled water containing 0.5% DMSO;
T50 = 110 hours The results show that corn seeds treated with compounds of the present invention exhibited faster (more negative T50) and more synchronous (more positive slope) germination than prior art compounds.

The invention claimed is:

1. A compound of formula (I)

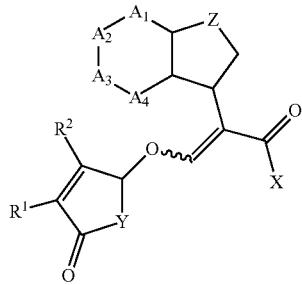

(I)

wherein
$R^1$ and $R^2$ are independently selected from the group consisting of hydrogen, $C_1$-$C_3$ alkyl and $C_1$-$C_3$ alkoxy;
X is $O(R^3)$;
$R^3$ is selected from the group consisting of hydrogen and $C_1$-$C_4$ alkyl;
Y is O;
Z is selected from the group consisting of a bond, $CH_2$, $CH_2$-$CH_2$, $CH_2$ (wherein the oxygen atom is bonded to the carbon positioned alpha to the $A_1$ substituent) and oxygen;
$A_1$ to $A_4$ are each independently selected from the group consisting of a bond, $CR^8$, N, S and O, wherein $A_1$ to $A_4$ together with the atoms to which they are joined form a 5 to 6 membered aryl or heteroaryl; and
each $R^8$ is selected from the group consisting of hydrogen, halogen, methyl, ethyl, methoxy, ethoxy, fluoromethyl and trifluoromethyl; or two $R^8$ groups are joined via —$OCH_2O$—to form a dioxolane ring;
or salts thereof.

2. A compound according to claim 1, wherein $R^1$ and $R^2$ are independently selected from the group consisting of hydrogen, methyl, ethyl and methoxy.

3. A compound according to claim 1, wherein $R^1$ is methyl and $R^2$ is hydrogen or methyl.

4. A compound according to claim 3, wherein $R^2$ is methyl.

5. A compound according to claim 1, wherein $R^3$ is selected from the group consisting of hydrogen, methyl and ethyl.

6. A compound according to claim 1, wherein $A_1$ to $A_4$ are each independently selected from the group consisting of a bond, $CR^8$, N, S and O, and $A_1$ to $A_4$ together with the atoms to which they are joined form a 5 to 6 membered aryl or heteroaryl.

7. A compound according to claim 1, wherein $A_1$ to $A_4$ are each $CR^8$.

8. A composition comprising a compound according to claim 1, and an agriculturally acceptable formulation adjuvant.

9. A mixture comprising a compound as defined in claim 1, and a further active ingredient.

10. A crop yield enhancing composition, comprising a compound according to claim 1.

11. A method for improving the tolerance of a plant to abiotic stress, promoting seed germination of a plant, or regulating or improving the growth of a plant, wherein the method comprises applying to the plant, plant part, plant propagation material, or plant growing locus a compound according to claim 1.

12. A compound according to claim 1, wherein Z is $CH_2$.

13. A compound according to claim 1, selected from: ethyl (E)-2-indan-1-yl-3-[(4-methyl-5-oxo-2H-furan-2-yl)oxy]prop-2-enoate; ethyl (E)-3-[(3,4-dimethyl-5-oxo-2H-furan-2-yl)oxy]-2-indan-1-yl-prop-2-enoate; methyl (E)-2-indan-1-yl-3-[(4-methyl-5-oxo-2H-furan-2-yl)oxy]prop-2-enoate; methyl (E)-3-[(3,4-dimethyl-5-oxo-2H-furan-2-yl)oxy]-2-indan-1-yl-prop-2-enoate; ethyl (E)-2-(5,6-dimethoxyindan-1-yl)-3-[(4-methyl-5-oxo-2H-furan-2-yl)oxy]prop-2-enoate; ethyl (E)-2-(5,6-dimethoxyindan-1-yl)-3-[(3,4-dimethyl-5-oxo-2H-furan-2-yl)oxy]prop-2-enoate; ethyl (E)-2-(6,7-dihydro-5H-cyclopenta[f][1,3]benzodioxol-7-yl)-3-[(4-methyl-5-oxo-2H-furan-2-y 1)oxy]prop-2-enoate; ethyl (E)-2-(4-methylindan-1-yl)-3-[(4-methyl-5-oxo-2H-furan-2-yl)oxy]prop-2-enoate; ethyl (E)-3-[(4-methyl-5-oxo-2H-furan-2-yl)oxy]-2-[4-(trifluoromethyl)indan-1-yl]prop-2-enoate; ethyl (E)-3-[(3,4-dimethyl-5-oxo-2H-furan-2-yl)oxy]-2-(6-hydroxyindan-1-yl)prop-2-enoate; ethyl (E)-3-[(3,4-dimethyl-5-oxo-2H-furan-2-yl)oxy]-2-tetralin-1-yl-prop-2-enoate; ethyl (E)-2-(7-bicyclo[4.2.0]octa-l(6),2,4-trienyl)-3-[(4-methyl-5-oxo-2H-furan-2-yl)oxy]prop-2-enoate; ethyl (E)-2-(5,6-dihydro-4H-cyclopenta[b]thiophen-6-yl)-3-[(3,4-dimethyl-5-oxo-2H-furan-2-yl)oxy]prop-2-enoate; ethyl (E)-2-chroman-4-yl-3-[(4-methyl-5-oxo-2H-furan-2-yl)oxy]prop-2-enoate; ethyl (E)-2-chroman-4-yl-3-[(3,4-dimethyl-5-oxo-2H-furan-2-yl)oxy]prop-2-enoate; and ethyl (E)-2-(2,3-dihydrobenzofuran-3-yl)-3-[(3,4-dimethyl-5-oxo-2H-furan-2-yl)oxy]prop-2-enoate.

* * * * *